US00RE38073E

(19) United States
(12) Reissued Patent
Carpino

(10) Patent Number: US RE38,073 E
(45) Date of Reissued Patent: Apr. 8, 2003

(54) PRODUCTS FOR PEPTIDE COUPLING

(75) Inventor: Louis A. Carpino, Amherst, MA (US)

(73) Assignee: Research Corporations Technologies, Inc., Tucson, AZ (US)

(21) Appl. No.: 09/343,756

(22) Filed: Jun. 30, 1999

Related U.S. Patent Documents

Reissue of:
(64) Patent No.: 5,644,029
Issued: Jul. 1, 1997
Appl. No.: 08/468,300
Filed: Jun. 6, 1995

U.S. Applications:
(60) Division of application No. 08/127,675, filed on Sep. 28, 1993, now Pat. No. 5,580,981, which is a continuation-in-part of application No. 07/952,025, filed on Sep. 28, 1992, now abandoned.

(51) Int. Cl.[7] ..... C07K 1/10
(52) U.S. Cl. ..... 530/333; 530/334; 530/338; 530/339; 530/340; 530/341; 544/235; 544/253; 544/262; 554/35
(58) Field of Search ..... 530/333, 334, 530/338, 339, 340, 341; 544/235, 253, 262; 554/35

(56) References Cited

U.S. PATENT DOCUMENTS

| | | | | |
|---|---|---|---|---|
| 3,725,380 A | | 4/1973 | Konig et al. | 530/341 |
| 5,580,981 A | * | 12/1996 | Carpino | 544/262 |
| 5,644,029 A | * | 7/1997 | Carpino | 530/333 |

FOREIGN PATENT DOCUMENTS

| | | |
|---|---|---|
| EP | 0160546 | 11/1985 |
| EP | 0289353 | 11/1988 |
| EP | 0410182 | 1/1991 |

OTHER PUBLICATIONS

Przybylski, Roczniki *Chemii* 51, 939 (1977).

Gross, *The Peptides* vol. 2, pp. 125–127, 131–133 & 139–141 vol. 3, 261–265 (1980).

Jencks, Catalysis in Chem & Enzymology, 94 pp. 91 & 107–111, (1969).

Reese, J *Chem Soc Perk Trans* 1, 2291, (1993).

Cross, et al. "ipso Nitration. XXV. Nitration of di–tert–butylphenols. a –(3,5–di–tert–butylphenoxyacetic) isobutyric acid and 3,5–di–tert–butylphenoxyacetic acid: formation of nitrodienones and nitrodienes containing a secondary Nitro group", *Can. J. Chem.*, 62,2803–2812 (1984).

D'Anello, et al., "5–Oxazolones, II,2,4–Diaryl–4–(2,4–dinitroaryl)–5 (4H)–oxazolones: Synthesis and Acid Catalyzed Transformation into 1–Hydroxy–1H–indazole Derivatives", *Chem. Ber.* 121, 67–73 (1988).

Davis, et al. "Reactions of B–(Lithiomethyl) azines with Nitriles as a Routte to Pyrrolopyrimidines,–quinolines, pyrazines, –quinoxalines and –pyrimidines", *Tetrahedron*, 48, 939–952 (1992).

De Roos, et al., "Deazapurine Derivatives. VII. Syntheseis of substituted imidaza–and triazolopyridines." *Recueil*, 90, 1166–1180 (1971).

Biloski, et al., "Improved Oxidation of Amines with Dibenzoyl Peroxide", *Synthesis*, 537–538 (1989).

Chen, et al., "A New Coupling Reagent for Peptide Synthesis. Benzotriazolyloxy–Bis(Pyrrolidone)–Carbonium Hexafluorophosphate (BBC)", *Tetrahedron Letters*, 33, 647–650 (1992).

Clark, et al. "Preparation of Indoles and Oxindoles for N–(tert–Butoxycarbonyl)–2–alkylanilines", *Synthesis*, 871–878 (1991).

Coste, et al., "PyBOP: A New Peptide Coupling Reagent Devoid of Toxic By–Product", *Tetrahedron Letters*, 31, 205–208 (1990).

Hasimoto, et al., "A Multi–Centered Electrophile Formed From a Unique Bioactive Cyclic Hydroamic acid, 4–Hydroxy–7–Methoxy–2H–1, 4–Benzoxazin–3–(4H)–One", *Tetrahedron*, 47, 1837–1860 (1991).

Henklin, et al., "New uranium salt as a coupling reagents in peptide chemistry", *Peptides*, 67–68 (1990).

Kim, et al., "A Novel Synthesis of 1–OXA–HPMPA: A potent Antiviral Agent Against Herpesviruses", *Tetrahedron Letters*, 33: 25–28 (1992).

Kiso, et al., "Efficient Solid Phase Peptide Synthesis on a Phenacyl–Resin by Methane–Sulfonic Acid, α–Amino Deprotecting Procedure", *Chem. Pharm. Bull.*, 38, 270–272 (1990).

Knorr, et al. "New Coupling Reagents in Peptide Chemistry", *Tetrahedron Letters*, 30, 1927–1930 (1989).

Kundu, et al., "Racemization studies with 1–(β–naphthalenesulfonyloxy)–benzotriazole (NSBT)–An efficient peptide coupling reagent", *Indian Journal of Chemistry*, 28B 604–605 (1989).

Laus, et al., "Synthesis of 1–Amino–1H–1,2,4–triazoles", *Synthesis*, 269–272 (1989).

(List continued on next page.)

*Primary Examiner*—Christopher S. F. Low
*Assistant Examiner*—David Lukton
(74) *Attorney, Agent, or Firm*—Scully, Scott, Murphy & Presser

(57) ABSTRACT

This invention relates to a process for forming an amide or an ester from a reaction between an amine or an alcohol, respectively and an acylating derivative of a carboxylic acid, in the presence of an effective amount of a compound having the formula:

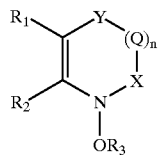

and N-oxides thereof and salts thereof.

202 Claims, No Drawings

OTHER PUBLICATIONS

Mahadevan, et al., "Synthesis of Pyrrolopyridines (Azaindles)", *J. Heterocyclic Chem.*, 29, 359–367 (1992).

Quiroz, et al., "Reaction of 7–Substituted 4–Hydroxyl–1, 4–Benzoxazin–3–Ones in Strongly Acidic Media", *Heterocycles*, 32, 1681–1685 (1991).

Takeda, et al., "A Convenient Synthesis of Peptide Using Oxallates", *Tetrahedron Letters*, 24, 4451–4454(1983).

Tanaka, et al., "Synthesis of Cyclic Hydroxamic Acid Derivatives and Their Chelating Abilities and Biological Activities", *Chem. Pharm. Bull.*, 36, 2323–2330(1988).

Azev, et al., "Structure and Properties of 1–and 3–Hydroxytriazolo [4,5–b] pyridines", *Chem. herterocycl. Cpds.*, (USSR) 1172–1176 (1976).

Sacher, et al., "Insecticidal and Anticholinesterase Activity of Benzotriazolyl Methyl and Dimethylcarbamates", *J. Agr. Food Chem.*, vol. 21. No. 1, 132–135 (1973).

Mokrushina, et al., "Reaction of 2–Nitro–3–fluorpyridine with Hydrazine", *Chem. Heterocycl. Cpds.*, (USSR) 880 (1975).

* cited by examiner

PRODUCTS FOR PEPTIDE COUPLING

Matter enclosed in heavy brackets [ ] appears in the original patent but forms no part of this reissue specification; matter printed in italics indicates the additions made by reissue.

RELATED APPLICATION

[This is] *This application is a reissue of application Ser. No. 08/468,300 filed Jun. 6, 1995, now U.S. Pat. No. 5,644,029 which is* a divisional of application Ser. No. 08/127,675, now U.S. Pat. No. 5,580,981, filed on Sep. 28, 1993 which is a continuation-in-part of U.S. Ser. No. 07/952,025 filed on Sep. 28, 1992, now abandoned.

GOVERNMENT SUPPORT

This work has been supported by a grant from the National Institutes of Health GM-09706 and the National Science Foundation (CHE-9003192). The Government has certain rights in the invention.

BACKGROUND OF THE INVENTION

1. Field of the Invention

The present invention relates to a new process for effecting the acylation step in amide formation, especially during peptide synthesis. More specifically, the invention relates to the use of a compound having the formula

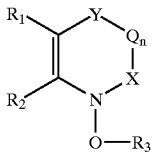

and N-oxides thereof and salts thereof wherein $R_1$ and $R_2$ taken together with the carbon atoms to which they are attached form a heteroaryl ring wherein said heteroaryl ring is an oxygen, sulfur or nitrogen containing heteroaromatic containing from 3 and up to a total of 13 ring carbon atoms, said heteroaryl may be unsubstituted or substituted with lower alkyl or an electron-donating group;

Y is O, $NR_4$, $CR_4R_5$;

$R_5$ is independently hydrogen or lower alkyl;

X is $CR_6R_7$ or $NR_6$;

$R_6$ or $R_7$ are independently hydrogen or lower alkyl; or $R_6$ and $R_7$ taken together form an oxo group or when n=O, $R_4$ and $R_6$ taken together may form a bond between the nitrogen or carbon atom of Y and the nitrogen or carbon atom of X;

Q is $(CR_8R_9)$ or $(NR_8)$;

when n is 1, $R_4$ and $R_8$ taken together may form a bond between the ring carbon or nitrogen atom of Q and the ring carbon or nitrogen atom of $R_8$;

n is 0, 1 or 2;

$R_3$ is hydrogen, lower alkyl carbonyl, aryl carbonyl, lower aryl alkyl carbonyl,

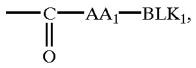

a positively charged electron withdrawing group, $SO_2$ $R_{14}$, or

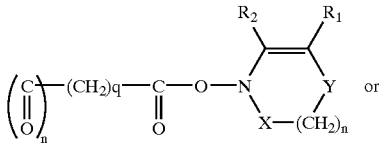

$R_{14}$ is lower alkyl, aryl or lower arylalkyl; q is 0–3;

$R_8$ and $R_9$ are independently hydrogen or lower alkyl or $R_7$ and $R_8$ taken together with the carbon to which they are attached form an aryl ring, $AA_1$ is an amino acid and BLK is an amino protecting group, and m is 0 or 1.

The present invention also relates to novel compounds encompassed by the above-identified formula.

2. Description of the Prior Art

Polypeptides are useful as medicaments. In recent years, peptides have been found to be useful in combatting various diseases, such as cancer, diabetes, plant toxins and the like. Additionally, peptides have shown specific activity as growth promoters, suppressants, antibiotics, insecticides, contraceptives, anti-hypertensives, sleep-inducers, antidepressants, analgesics, etc. The list is long and varied.

As more and more polypeptides become of medicinal importance, there is an increasing incentive to improve the methods by which they may be synthesized. Currently, syntheses of peptides are in solution by classical or various repetitive methods. Alternatively, peptides may be prepared on a solid support (Merrifield method). These are all popular techniques in synthesizing peptides from the coupling of two or more amino acids, in synthesizing larger peptides from the coupling of amino acids with smaller peptides or in the coupling of smaller peptides. Solution methods have the advantage of being easily monitored, allowing purification of intermediates, if necessary, at any stage. A major drawback, however, is the relative slow pace of synthesis, with each step being carried out manually.

The major advantage of the Merrifield method is its easy automation so that unattended, computer-controlled machine synthesis is possible. Unfortunately, the method suffers from an inherent deficiency due to the insoluble nature of the support on which the synthesis proceeds. Unless each acylation step occurs with approximately 100% efficiency, mixtures will inevitably be built up on the polymer. The longer the chain, the greater will be the contamination by undesired side reactions. Side products produced in such reactions remain to contaminate the desired product when it is removed from the polymeric matrix at the end of the cycle. These current techniques are not useful in preparing peptides of greater than 20–30 residues; separation of side products from the desired product becomes increasingly difficult when larger peptides are synthesized.

For very long segments (50 or more amino acids), therefore, current methods are not satisfactory. Often, mixtures are obtained of such forbidding complexity that it may be difficult or impossible to isolate the desired peptide.

The problems enumerated hereinabove may be eliminated if the proper derivatives of the underlying amino acids and/or the proper conditions for the coupling reaction could be found. Protecting groups, such as t-butyloxy-carbonyl (t-Boc) or N-α-(9-fluorenylmethyl)oxycarbonyl (Fmoc), have been used to minimize side reactions. But, additionally, other aspects of the coupling reaction must also be taken into consideration, such as the peptide coupling additive to be used in the coupling reaction.

Additives generally inhibit side reactions and reduce racemization. Heretofore, the most common peptide coupling additive used during peptide coupling for both solutions and solid phase syntheses is 1-hydroxybenzotriazole (HOBt). This reagent has been used either in combination with a carbodimide or other coupling agent or built into a stand-alone reagent, such as 1-benzotriazolyoxytris (dimethylamino)phosphonium hexafluorophosphate (BOP) or an analogous uronium salt. HOBt is applicable to both stepwise and segment condensations. However, many cases have been encountered in which HOBt is ineffective, possibly because of steric effects, or low basicity of the amino component. Especially problematic are segment couplings at amino acid units other than glycine or proline, since the problem of racemization may be severe. The related N-hydroxybenzotriazinone (HOOBt) may provide better protection against recemization, but it is rarely used due to competing side reactions involving ring openings.

However, the present inventor has discovered that compounds of Formula I are effective as peptide coupling additives in both stepwise (batch and continuous flow) and segment condensations to peptide syntheses. Compounds of Formula I overcame deficiencies of the additives used heretofore. Compounds of the present invention, as a peptide coupling additive, have the ability to accelerate the reaction, or provide cleaner processes, higher yields and less racemization. The products formed with the use of compounds of the present invention tend to be purer than those made by methods used heretofore. Yet, the reaction conditions are very mild, and the reagents used are commercially available and/or easy to prepare.

Furthermore, compounds within the scope of the present invention have an additional benefit and provide a visual indication of the reaction endpoint. For example, HOAt or 1-hydroxy-7-azabenzotriazole in the presence of an amino acid or peptide ester, is converted to its anion, which is colored. As coupling proceeds, the color fades and then disappears completely when the coupling reaction is completed. By watching for the disappearance of the color, the researcher knows when the coupling reaction is completed. The researcher does not need to monitor the reaction to determine when the coupling reaction is completed. He does not need to wait an unspecified amount of time for the reaction to be completed. Thus, by using the compound of the present invention the researcher, as a result, can use his time more efficiently.

BRIEF DESCRIPTION OF THE INVENTION

The present invention relates to the use of a compound of Formula I in peptide synthesis in the preparation of a peptide bond. More specifically, the present invention relates to a process for preparing a peptide bond which comprises reacting a first amino acid or a first peptide each having a free amino group with a second amino acid or a second peptide, each having a free carboxy group or an acylating derivative thereof in the presence of an effective amount of a compound having Formula I under amide forming conditions. In addition, the present invention is directed to novel compounds of Formula I.

DETAILED DESCRIPTION OF THE PRESENT INVENTION

As described hereinabove, an embodiment of the present invention relates to compounds of Formula I and their use in peptide coupling. In other words a first amino acid or a first peptide, each having a free amino group is coupled with an acylating derivative of either a second amino acid or a second peptide in the presence of compounds of Formula I under amide forming conditions to form a peptide bond and thus form a larger peptide.

As employed herein, the term "heteroaryl" is a heteroaromatic containing at least one heteroatom ring atom selected from nitrogen, sulfur and oxygen and up to a maximum of four ring heteroatoms. The heteroaryl contains from 5 to 14 ring atoms and up to a total of 13 ring carbon atoms and a total of 18 carbon atoms. The heteroaryl group may be monocyclic, bicyclic or tricyclic. Also included in this expression are the benzoheterocyclic. The heteroaryl group preferably contains no more than two ring heteroatoms, and most preferably contains one ring heteroatom. The most preferred ring heteroatoms are oxygen and nitrogen, with nitrogen being the most preferred.

If nitrogen is a ring atom, N-oxides can also be formed. The present invention contemplates the N-oxides of the nitrogen containing heteroaryls.

Examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, isothiazolyl, isoxazolyl and the like. It is preferred that the heteroaryl group is pyridyl, pyrrolyl, furyl, indolyl, quininolyl, isoquinolyl or benzofuryl. Especially preferred is pyridyl.

When $R_1$ and $R_2$ taken together with the carbons to which they are attached form a tricyclic heteroaryl group, then the compounds of Formula I is tetracyclic; if a bicyclic heteroaryl group is formed from $R_1$ and $R_2$ taken together with the carbons to which they are attached, then the compounds of Formula I are tricyclic. Finally, if $R_1$ and $R_2$ taken together form a monocyclic heteroaryl group, then the compounds of Formula I are bicyclic. It is preferred that compounds of Formula I are tricyclic, and especially bicyclic.

The term "alkyl", when used alone or in combination with other groups, refers to a carbon chain containing from one to six carbon atoms. It may be a straight chain or branched and includes such groups as methyl, ethyl, propyl, isopropyl, n-butyl, sec-butyl, isobutyl, t-butyl, n-pentyl, amyl, hexyl and the like. The preferred alkyl group contains from 1–3 carbon atoms, and most preferably methyl.

The term "aryl" as used herein, alone or in combination, refers to an aromatic ring system containing from 6–10 ring carbon atoms and up to a total of 15 carbon atoms. It includes such groups as phenyl, α-naphthyl, β-naphthyl and the like.

Aralkyl groups are aryl groups attached to the main chain through an alkylene bridge. Such groups include benzyl, phenethyl and the like.

Alkyl carbonyl refers to an alkyl group attached to the main chain through a carbonyl. Similarly, aryl carbonyl refers to an aryl group attached to the main chain through a carbonyl group.

As used herein, an "electron donating group" shall designate a group that will release or donate electrons more than hydrogen would if it occupied the same position in the molecule. See J. March, Advanced Organic Chemistry, 3rd Ed., John Wiley & Sons p. 238 (1985). These types of groups are well known in the art. Examples include lower alkylamino, diloweralkylamino, amino, halo, aryl, lower alkoxy, lower aralkoxy, aryloxy, mercapto, lower alkylthio, and the like. The preferred electron donating groups are amino, hydroxy, lower alkoxy, lower alkylamino and dilower-alkylamino.

The term "electron withdrawing groups" as defined herein refer to a group that will draw electrons to itself more than a hydrogen atom would if it occupied the same position in the molecule. See, J. March, Advanced Organic Chemistry, 3rd Ed., John Wiley & Sons P. 17 (1985). They include such groups as nitro, monophaloalkyl, dihaloalkyl, trihaloalkyl (e.g., $CF_3$), halo, formyl, lower alkanoyl, lower alkylsulfonyl, lower alkylsulfinyl, and the like.

A positively charged electron withdrawing group is an electron withdrawing group bearing a positive charge and forming a stable bond to a N-hydroxide (N—O). These types of groups are well known in the art. Examples include uronium groups, e.g.,

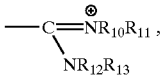

imino cations e.g.,

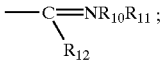

phosphonium cations, e.g., $—P^{\oplus}(NR_{12}R_{13})_3$ and the like, wherein $R_{10}$, $R_{11}$, $R_{12}$ and $R_{13}$ are independently hydrogen or lower alkyl, lower alkoxy lower alkyl or $R_{10}$ and $R_{12}$ taken together with the atoms to which they are attached form a ring containing up to 6 ring atoms and up to a total of 5 ring carbon atoms or $R_{12}$ and $R_{13}$ taken together with the nitrogen atom to which they are attached may form a 5 or 6 membered heterocyclic ring containing up to a total of 5 ring carbon atoms. It is preferred that $R_{10}$ and $R_{11}$ and $R_{12}$ and $R_{13}$, when both are present, are the same. It is especially preferred that $R_{10}$, $R_{11}$, $R_{12}$, $R_{13}$, when ever are present, are the same.

Preferred cyclic uronium and imino groups have the formula

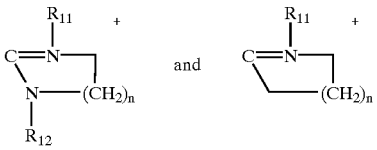

respectively, wherein $R_{11}$ and $R_{12}$ are as defined hereinabove and n is 0 or 1.

In the above formulae, the preferred values of $R_{10}$, $R_{11}$, $R_{12}$ and $R_{13}$ are methyl, ethyl, n-butyl, pentyl and $—CH_2CH_2—O—CH_2CH_3$. It is preferred that $R_{11}$ and $R_{12}$ are the same.

The preferred values of $R_{12}$ and $R_{13}$ are lower alkyl, especially methyl. It is preferred that both $R_{12}$ and $R_{13}$ are both the same. Further, it is preferred that both are methyl.

When $R_{12}$ and $R_{13}$ taken together form a ring, they may form heterocyclic moieties of the formula:

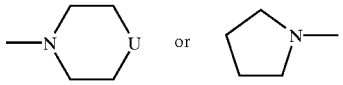

wherein $U=CH_2$, O, or N-Alk, wherein Alk is lower alkyl, especially methyl.

It is preferred that $R_7$ and $R_8$ are hydrogen or lower alkyl, but most preferably hydrogen.

Preferred values of Y are S, O, $NR_4$ or $CR_4R_5$, wherein $R_4$ and $R_5$ are independently hydrogen or methyl. Especially preferred values of Y are O, $CH_2$ or NH.

It is preferred that X is $CR_6R_7$ or $NR_6$. Preferred values of $R_6$ and $R_7$ are hydrogen or lower alkyl. When $R_6$ and $R_7$ taken together form an oxo group, X becomes C=O. It is most preferred that X is C=O, $CH_2$ or NH or $N(CH_3)$. However, in cases when n is 0, then $R_4$ and $R_6$ taken together may form a bond between X and Y, i.e., a bond may form between the ring carbon atoms of X and the ring carbon atom of Y, or between the ring nitrogen atom of X and the ring nitrogen atom of X, or the ring nitrogen atom of X, and the ring carbon atom of Y or the ring carbon atom of X and the ring nitrogen atom of Y. In other words, under these circumstances, the compound of Formula I becomes

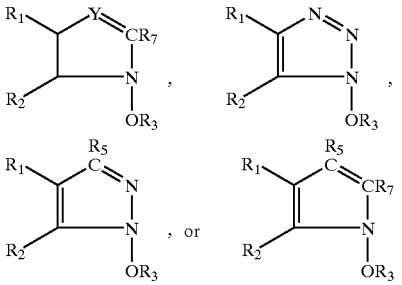

wherein $R_1$, $R_2$, Y, X, and $R_3$ are as defined above. Under these circumstances, it is preferred that Y is CH or N and X is CH or N. It is most preferred that Y and X are N.

When n is 1, the compound of Formula I becomes

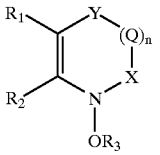

wherein

Q, $R_1$, $R_2$, Y, $R_8$, $R_9$ X and $R_3$ are as defined above. It is preferred that $R_8$ and $R_9$ are hydrogen.

As indicated hereinabove, when n is 1, $R_4$ and $R_8$ taken together may form a bond between Q and Y, i.e., the ring carbon atom of $R_4$ and the ring carbon atom of $R_8$ may form a bond, or the ring carbon atom of $R_4$ and the ring nitrogen atom of $R_8$ may form a bond, or the ring nitrogen atom of $R_4$ and the ring carbon atom of $R_8$ may form a bond or the ring nitrogen atom of $R_4$ and the ring nitrogen atom of $R_8$ may form a bond. In other words, under these circumstances, the formula becomes:

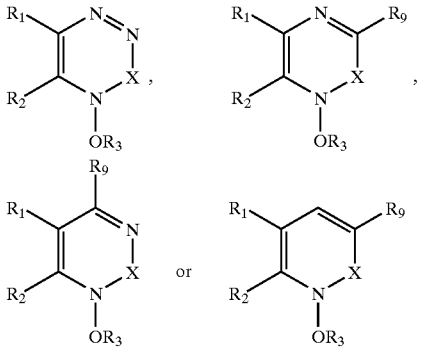

Preferred values of Y in this formulation are S, O $CH_2$ or N—H or N—($CH_3$). It is most preferred under these circumstances that Y is S, O or N($CH_3$).

The preferred values of X in this formulation are C═O or NH or $CH_2$.

Preferred values of Q are $CH_2$ or NH. However, it is also preferred that the above-identified compound has the formula:

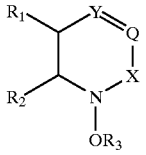

wherein

Q is $CR_9$ or N, $R_9$ is hydrogen or lower alkyl and $R_1$, $R_2$, X, $OR_3$ are as defined hereinabove. Examples of the above formula include:

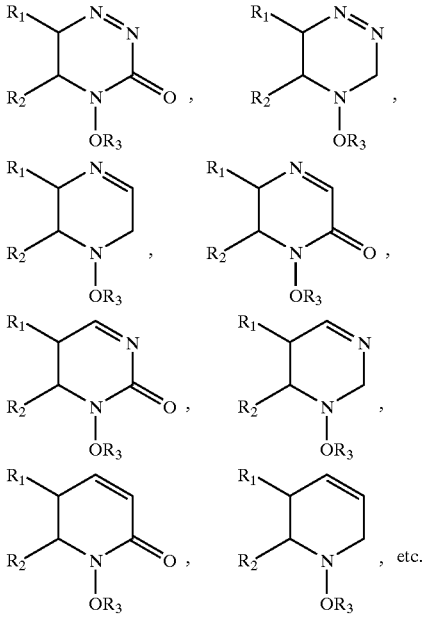

It is also preferred that compounds of Formula I have the formula:

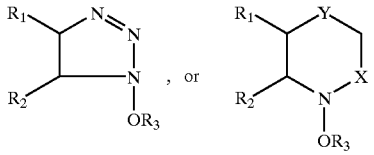

wherein $R_1$, $R_2$, $R_3$, Y and X are as defined hereinabove.

Preferred compounds of Formula I have the formula:

II

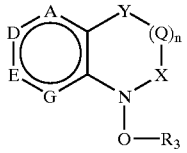

or N-oxides thereof wherein

Q, Y, X, $R_3$, n, $R_4$, $R_5$, $R_6$, $R_7$, $R_8$, $R_9$ and $R_{14}$ are as defined hereinabove, A is N or $CR_{15}$;

D is $CR_{16}$ or N;

E is $CR_{17}$ or N;

G is $CR_{18}$ or N; and $R_{15}$, $R_{16}$, $R_{17}$ and $R_{18}$ are independently hydrogen or lower alkyl or an electron donating group or $R_{16}$ and $R_{17}$ taken together form an aryl ring, but at least one of A, D, E, G is N.

It is preferred that no more than two of A, D, E, G are N. It is most preferred that only one of A, D, E, G is N. Further, it is preferred that $R_{15}$, $R_{16}$, $R_{17}$ or $R_{18}$ are hydrogen or an electron-donating group, as defined herein. The preferred electron donating group is lower dialkylamino especially N, N-dimethyl-amino and lower alkoxy, e.g. methoxy.

Preferred compounds of Formula II have the formulae:

III

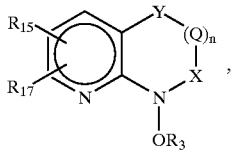

IV

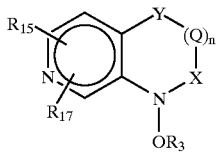

V

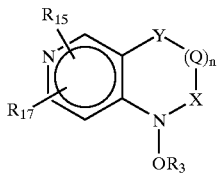

-continued

VI

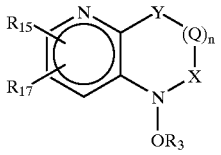

or N-oxides thereof wherein Y, X, n, Q and $R_3$ are as defined hereinabove and $R_{15}$ and $R_{17}$ are independently lower alkyl and more preferably hydrogen or an electron donating group.

Of the compounds of Formula III–VI, the most preferred compound is that of Formula IIIa IIIa

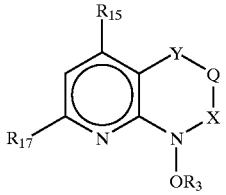

or N-oxides thereof wherein Q, Y, X and $R_3$ are as defined hereinabove and $R_{15}$ and $R_{17}$ are lower alkyl or hydrogen or an electron withdrawing group.

Preferred compounds of Formula I also have the formula

VII

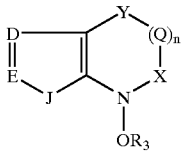

or

VIII

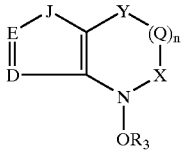

or N-oxides thereof wherein $R_8$, $R_9$, n, Q, D, E, X and Y are as defined hereinabove and J is $NR_{15}$, O, $CR_{15}R_{19}$ or S(O)p, and p is 0, 1, 2.

$R_{15}$ is as defined hereinabove and $R_{19}$ is hydrogen or lower alkyl. It is preferred that $R_{19}$ is hydrogen, and preferred values of $R_{15}$ is an electron donating group or hydrogen.

Preferred values of J are O or S(O)p; the preferred value of p is 1.

Preferred compounds of Formula VII have the formula:

VIIa

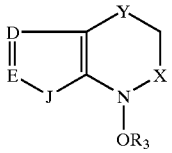

or N-oxides thereof wherein J, Y, $R_8$, $R_9$ n and $R_3$ are as defined hereinabove and X is C═O.

In compounds VII, VIII or VIIa as depicted above, it is preferred that at least one of D, E or J is a heteroatom. Furthermore, it is most preferred that at most two of J, E and D are heteroatoms. It is most preferred that only one of J, E and D is a heteroatom.

Thus, the present invention includes compounds having the formula:

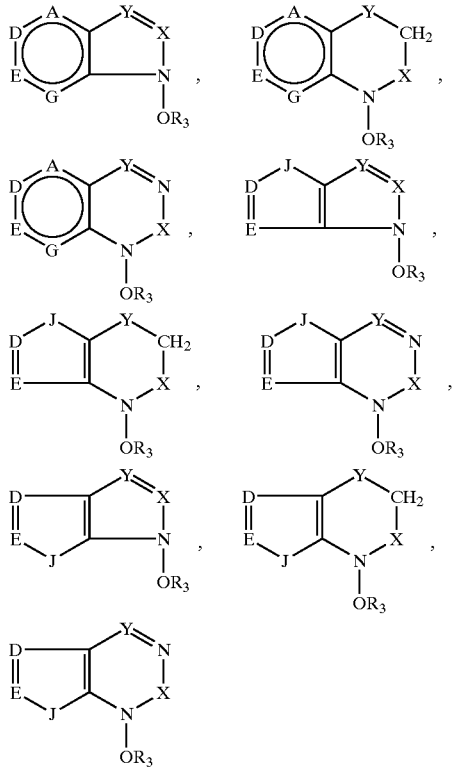

or N-oxides thereof wherein A, D, E, G, Y, X, $R_3$ and J are as defined hereinabove.

Furthermore, the present invention includes use of compounds of the formula

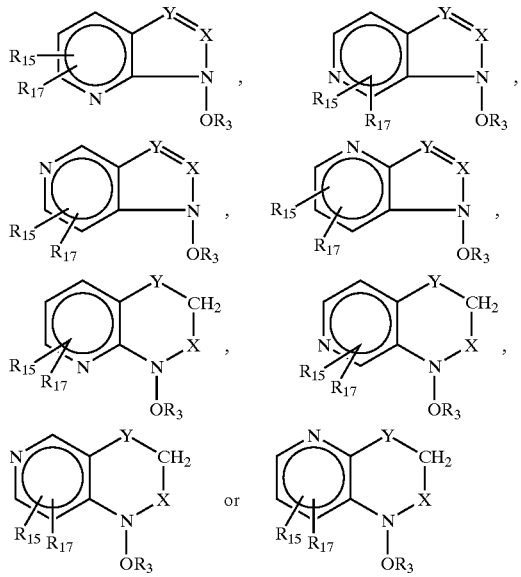

or

-continued

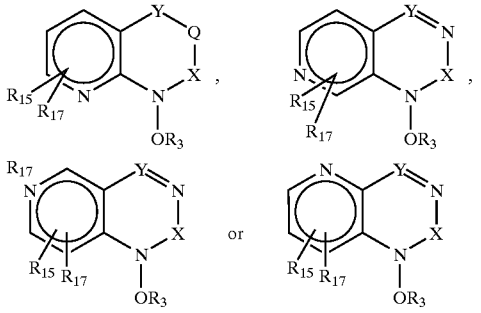

or N-oxides thereof.

In the above formulae, when the ring contains Y═X, this means that $R_4$ of Y and $R_6$ of X are joined together to form a ring bond between the Y ring atom and the X ring atom, so that as depicted hereinabove there is a double bond between the Y ring atom and the X ring atom. Furthermore, in the above formulae, when the ring contains Y═N, then $R_4$ of Y and $R_8$ of $NR_8$ of Q joined together to form a ring bond so that there is a double bond between the nitrogen ring atom and the Y atom. Thus, Y is $CR_5$ or N under these circumstances.

Preferred embodiments of compounds of Formula I include

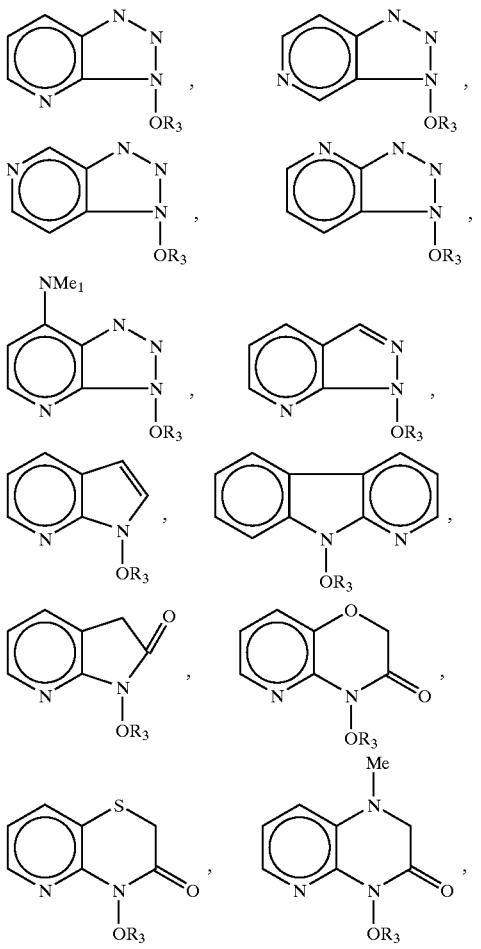

-continued

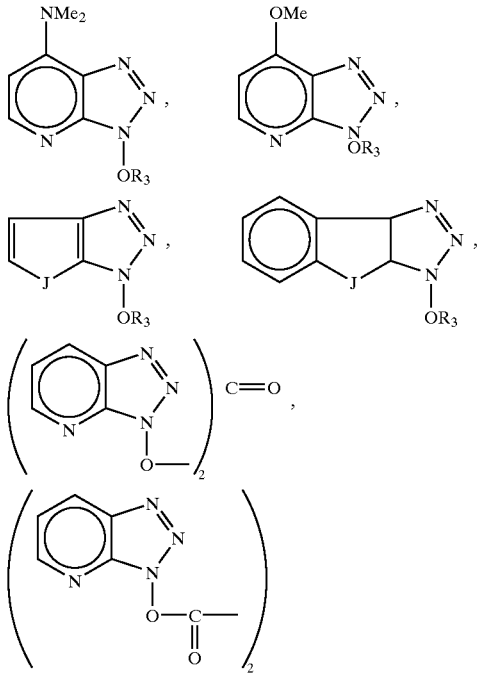

or the N-oxides thereof wherein $R_3$ is H, $P^{\oplus}$—$(NR_{10})_3$,

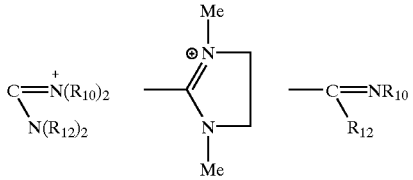

$R_{10}$ and $R_{12}$ are independently methyl, ethyl, propyl, butyl, pentyl $CH_2CH_2O$—$CH_2CH_3$, $R_{15}$ is Me, Et, i-Pr, $iPr_2N$, or $CMe_3$ J is O, or S(O)p, and p is 0, 1 or 2.

Of course, various combinations and permutations of the formulae described herein are also contemplated by the present invention. In addition, Markush groupings containing less than all of the elements described hereinabove as well as the various permutations thereof are also contemplated by the present invention.

As described herein, the compounds described hereinabove are useful in promoting peptide coupling, i.e., the reaction between a free amino group of a first amino acid or first peptide with a free carboxy group or acylating group of a second amino acid or peptide. The process of the present invention is general; it can be used in effecting the coupling of a dipeptide and an amino acid, a tripeptide and an amino acid, a tetrapeptide and an amino acid, dipeptides, pentapeptides, higher peptides, polypeptides etc.

When the compound of Formula I reacts with an amino compound such as an amino blocked amino acid or protein of the formula $BLK_1$-$AA_1$ the corresponding amino acid ester of the formula is formed, i.e.,

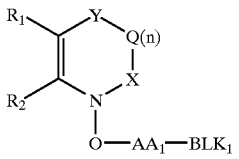

wherein $AA_1$ is an amino acid or protein as defined herein, $BLK_1$ is a blocking group as defined herein and Y, Q, n, X, $R_1$, and $R_2$ are as defined hereinabove. This amino acid ester can then react with a compound having a free amino, such as an arylamino, alkylamino, lower aryl amino, etc. designated as $R_{21}R_{22}$, NH, wherein $R_{21}$ and $R_{22}$ are independently hydrogen, lower alkyl, aryl or lower aryl alkyl to form a compound of the formula:

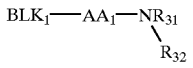

Removal of the blocking group by techniques known to one skilled in the art affords the product:

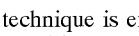

This technique is extremely useful when the second amino compound is an amino acid or peptide having a free amine group, designated as $AA_2$. In this case, a peptide is formed between $AA_1$ and $AA_2$; for example,

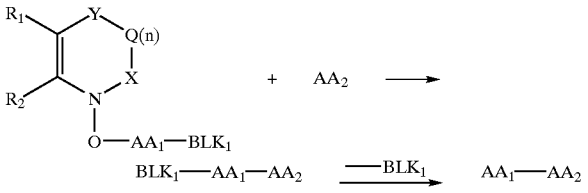

wherein $AA_1$, $AA_2$, $BLK_1$, $R_1$, R, Y, Q, n and X are as defined herein.

As with most peptide coupling reactions, a dehydrating agent, such as EDC or DCC can be present.

The blocking group can be any of the blocking groups described herein, but the preferred blocking groups are FMOC, BOC, benzyloxycarbonyl BSMOC and Bspoc.

The term "amino acid" or AA, $AA_1$, or $AA_2$ as used herein refers to an organic acid containing both a basic amino group ($NH_2$) and an acidic carboxyl group. (COOH). Therefore, said molecule is amphoteric and exists in aqueous solution as dipole ions. (See "The Condensed Chemical Dictionary", 10th Ed., edited by Gessner G. Hawley, Van Nostrand Reinhold Company, London, England p. 48 (1981). The preferred amino acids are the α-amino acids. They include but are not limited to the 25 amino acids that have been established as protein constituents. They must contain at least one carboxyl group and one primary or secondary amino group in the amino acid molecule. The term includes such proteinogenic amino acids as alanine, valine, leucine, isoleucine, norleucine, proline, hydroxyproline, phenylalanine, tryptophan, amino, subutryic acid, methionine, glycine, serine, threonine, cysteine, cystine, glutamic acid, lysine, hydroxylysine, ornithine, arginine, histidine, penicillamine, naphthylamine, α-phenylglycine, and the like.

As used herein, the term "peptide" refers to the class of compounds composed of amino acid units chemically bound together with amide linkages. A peptide may contain as little as two amino acid residues or may contain a polymer of amino acid residues (polypeptide).

As used herein, the terms "amino acid" and "peptide" also include amino acids and peptides, respectively containing blocking (protecting) groups. These protecting "groups" block the amino group or the carboxyl group of the amino acid or peptide not involved in or taking part in the coupling in order to prevent unwanted side reactions. These protecting groups also protect reactive groups on the side chain.

A number of blocking reagents for amino groups are known in the art and have been utilized in the syntheses of peptides. These blocking groups are discussed in U.S. Pat. Nos. 3,835,175, 4,508,657, 3,839,396, 4,581,167, 4,394,519, 4,460,501 and 4,108,846, the contents of all of which are incorporated by reference as if fully set forth herein. Other amino protecting groups are discussed in U.S. patent application Ser. No. 364,662, now abandoned, the contents of which are also incorporated by reference. Other amino protecting groups are described in an article entitled "Solid Phase Peptide Synthesis", by G. Barany and R. B. Merrifield in THE PEPTIDES, Vol. 2, edited by E. Gross and J. Meienhoffer, Academic Press, N.Y., N.Y. 100–118 (1980), and in the book entitled "PROTECTIVE GROUPS IN ORGANIC SYNTHESIS" by T. W. Green, John Wiley & Sons, New York, the contents of all of which are being incorporated by reference.

The term amino acid protecting group, (BLK, BLK,) as used herein, refers to blocking groups which are known in the art and which have been utilized to block the amino ($NH_2$) group of the amino acid. Blocking groups such as 9-lower alkyl-9-fluorenyloxycarbony,2-chloro-1-indanylmethoxy-carbonyl (CLIMOC) and benz[f]indene-3-methyloxycarbonyl (BIMOC) and dbd-TMOC are discussed in U.S. Pat. Nos. 3,835,175, 4,508,657, 3,839,396, 4,581,167, 4,394,519, 4,460,501 and 4,108,846 referred to hereinabove. Moreover, other amino protecting groups such as 2-(t-butyl sulfonyl)-2-propenyloxycarbonyl (Bspoc) and benzothiophene sulfone-2-methoxycarbonyl (Bsmoc) are discussed in copending application, U.S. patent application Ser. No. 364,662, now abandoned, the contents of which are incorporated herein by reference. Other N-amino protecting groups include such groups as the t-butyloxycarbonyl (BOC), t-amyloxycarbonyl (Aoc), β-trimethylsilylethyloxycarbonyl (TEOC), adamantyloxycarbonyl (Adoc), 1-methylcyclobutyloxycarbonyl (Mcb), 2-(p-biphenylyl) propyl-2-oxycarbonyl (Bpoc), 2-(p-phenylazophenyl) propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), p-toluenesulfonyl aminocarbonyl (Tac), o-nitrophenylsulfenyl (Nps), dithiasuccinoyl (Dts), Phthaloyl, piperidine-oxycarbonyl, formyl, trifluoroacetyl and the like.

These protecting groups can be placed into four categories:

1) a base labile Nα-amino acid protecting group such as FMOC, and the like.
2) protecting groups removed by acid, such as Boc, TEOC, Aoc, Adoc, Mcb, Bpoc, Azoc, Ddz, Poc, Cbz, 2-furanmethyloxycarbonyl (Foc), p-methoxybenzyloxycarbonyl (Moz), Nps, and the like.
3) protecting groups removed by hydrogenation such as Dts, Cbz.
4) protecting groups removed by nucleophiles, such as Bspoc, Bsmoc and Nps and the like.

5) protecting groups derived from carboxylic acids, such as formyl, acetyl, trifluoroacetyl and the like, which are removed by acid, base or nucleophiles.

A variety of carboxy protecting groups known in the art may be employed. Examples of many of these possible groups may be found in "Protective Groups in Organic Synthesis", by T. W. Green, John Wiley & Sons, 1981, the contents of which is incorporated by reference. These examples include such groups as methyl ester, t-butyl ester, β-trimethylsilylethyl ester, benzyl ester and the like.

[In addition, during the course of protein synthesis, it may be necessary to protect certain side chains of the amino acids to prevent unwanted side reactions. The various protecting groups are discussed in the contents of which are incorporated herein by reference.]

*In addition, during the course of protein synthesis, it may be necessary to protect certain side chains of the amino acids to prevent unwanted side reactions. The various protecting groups are discussed in copending U.S. patent application Ser. No. 426,121 now U.S. Pat. No. 5,360,928, the contents of which are incorporated herein by reference.*

The term "acylating group of an amino acid or peptide" refers to a group on the free carboxy end of the amino acid or peptide that facilitates the acylation reaction, i.e., nucleophilic substitution at the acyl carbon. Examples include the free acid, acid halide, esters, such as lower alkyl esters, phenoxy esters which are unsubstituted or substituted with 1–5 electron withdrawing groups as defined herein; or an anhydride and the like. The preferred acylating derivative is the acid, acid halide, especially the acid chloride or fluoride, and the phenoxy ester.

The preferred acylating amino acid is an amino acid group of the formula

BLK-AA-M, wherein

BLK is an amino protecting group

AA is an amino acid and

M is halo or

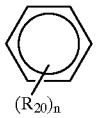

wherein $R_{20}$ is independently halo, lower alkyl, nitro, cyano or other electron withdrawing groups and n is 0–5. When n is 0, the phenoxy ester is unsubstituted.

The most preferred acylating group of an amino acid is the amino acid chloride or fluoride. The preparation and use of amino acid chlorides as an acylating derivative is discussed in an article by Carpino, et al. in J. Org. Chem., 1986, 51, 3734–3736, the contents of which are incorporated herein by reference. Briefly, amino acid chlorides can be prepared by reacting the amino acid with thionyl chloride and recrystallizing the product from a recrystallization reagent, such as $CH_2Cl_2$-hexane.

The preparation and use of amino acid fluorides in peptide synthesis are discussed in the contents of which are incorporated herein by reference. As described therein, the amino acid fluorides can be prepared by reacting an N-protected amino acid with the reagent cyanuric fluoride. This reaction can be run at temperatures as low as 0° C. and up to the refluxing temperature of the solvent, but it is preferred that the reaction is run at room temperature. It can also be run in an inert solvent, such as pyridine/$CH_2Cl_2$ and the like. The cyanuric fluoride can be prepared from the corresponding chloride in the presence of potassium fluoride at elevated temperatures ranging from 150° to 250° C., according to the following equation

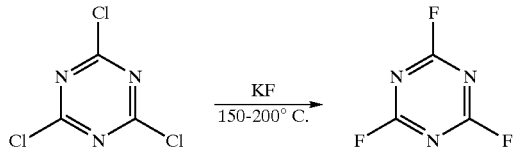

Other fluorinating agents well known in the art, such as thionyl fluoride, 2,4,6-trinitrofluorobenzene, N-methyl-2-fluoropyridinium salts, and the like may be used in place of KF to effect the formation of cyanuric fluoride.

A typical preparation of the peptide in accordance with the present invention involves the following steps 1) protection of the free carboxyl group in a first amino acid or a first peptide, unless the amino acid or peptide is anchored to a solid support.

2) protection of the free amino group of a second amino acid or peptide.

3) protection of the side chains, if necessary.

4) coupling the first amino acid or peptide with the second amino acid or peptide in the presence of compounds of Formula I.

5) removal of the protecting groups.

The procedure of steps 1–3 can be performed in any order.

In the coupling step, the compounds of Formula I should be present in effective amounts. Usually, the first amino acid or peptide is present in approximately equimolar amounts with the second amino acid or peptide, although the reaction can take place if the molar ratio of the former to the latter ranges from 1:3 to 3:1. Furthermore, the amount of the compound having Formula I used depends upon the amount of peptide or amino acid which is present in the least amount (i.e. the limiting reagent); thus the molar ratio of the compound of Formula I to the amino acid or peptide ranges from 1:3 to 3:1 relative to the amino acid or peptide present in the least molar amount, although it is preferred that approximately equimolar amounts of the compound of Formula I, the first amino acid or peptide and the second amino acid or peptide be used.

The coupling reaction described hereinabove can take place in the additional presence of a dehydrating agent such as DCC (dicyclohexylcarbodiimide) or EDC, (N-ethyl-N'-(3-dimethylaminopropyl)carbodiimide hydrochloride) and the like. The coupling reaction usually takes place in an inert organic solvent such as dimethylformamide (DMF) or ethers, such as ethyl ether, THF or dioxane. In fact DMF is the preferred solvent in the solid phase synthesis because of its favorable solvation properties. The reaction takes place under mild conditions usually ranging from about 0° C. to about 30° C. After the peptide is formed, the blocking groups are removed by techniques known to one skilled in the art.

The following sequence is illustrative of the coupling reaction; in the examples below, amino acids (AA) are used, although the procedure is general for amino acids and/or peptides:

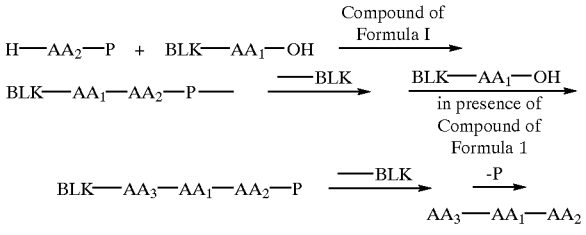

In the above scheme, BLK is an amino acid blocking group, $AA_1$, $AA_2$ and $AA_3$ are first, second and third amino acid, respectively and P is a carboxy protecting group.

As shown by the above scheme, the N-α amino protected amino acid is reacted with a second amino acid in which the carboxy group is protected.

A peptide is formed between the first amino acid and the second amino acid. The peptide chain can be increased by removing the alpha amino protecting group by techniques known to one skilled in the art and then reacting the corresponding dipeptide with another N-α amino protected amino acid in the presence of a compound of Formula I to form the corresponding tri-peptide. The N-α amino protecting group of the tri-peptide is removed and the above-cycle is repeated until the desired peptide has been obtained.

The present invention can readily be utilized in solid phase peptide synthesis. Solid phase peptide synthesis is based on the stepwise assembly of a peptide chain while it is attached at one end to a solid support or solid phase peptide resin. Two methods are generally well known in the art.

One, the Merrifield method, employs a solid support for attachment of the amino acid or peptide residues. This method employs N-protected amino acids as building blocks which are added to an amino acid or peptide residue attached to the solid support at the acyl (acid) end of the molecule. After the peptide bond has been formed, the protected group is removed and the cycle repeated. When a peptide having the desired sequence has been synthesized, it is then removed from the support.

The second method, the inverse Merrifield method, employs reagents attached to solid supports in a series of columns. The amino acid or peptide residue is passed through these columns in a series to form the desired amino acid sequence.

These methods are well known in the art as discussed in U.S. Pat. Nos. 4,108,846, 3,839,396, 3,835,175, 4,508,657, 4,623,484, 4,575,541, 4,581,167, 4,394,519 as well as in Advances in Enzymology, 32, 221 (1969) and in PEPTIDES, Vol. 2, edited by Erhard Gross and Johannes Meienhoffer, Academic Press, New York pp. 3–255 (1980) and the contents thereof are incorporated herein by reference as if fully set forth herein.

Without wishing to be bound, it is believed that the effectiveness of compounds of Formula I may be attributable to the neighboring group effect. More specifically, the super-nucleophilicity of the N-hydroxy group (N—O) may be enhanced by the neighboring group effect of the heteroatoms on the adjacent fused ring. For example, in HOAt, 1-hydroxy-7-azabenzotriazole, the super-nucleophilicity of the N-hydroxy group may be enhanced by the neighboring group effect of the pyridine nitrogen atom.

The compounds of Formula I can be prepared by art recognized techniques. The following example is exemplary:

Compounds of the formulae

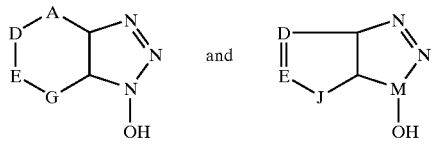

can be prepared by reacting hydrazine with

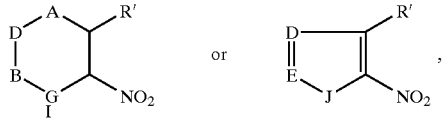

respectively wherein R' is halogen, NH—$NH_2$ or OR", $R^{11}$ is lower alkyl, such as methyl. This reaction is performed at slightly elevated temperatures, such as 70°–100° C., although the reaction may be performed at temperatures ranging from room temperature to the boiling point of the solvent.

The reaction is usually run in an organic solvent in which the reactants are insoluble at room temperature, but in which the reactants and product are soluble at slightly elevated temperatures. Examples of the solvent include ethanol, DMF and the like. In many cases, there is a color change in the reaction mixture, indicating the formation of the product. Work-up, such as removal of the solvent, followed by acidification provides the desired product.

The hydrazino derivative ($R^1$=NH—$NH_2$) of 1 and 2 can be prepared by reacting the corresponding halide, such as chloride or bromide, with hydrazine under substitution reaction conditions. The ether derivative ($R^1$=OR") of 1 and 2 can be prepared by reacting the corresponding alcohol with an alkylating reagent, such as $Me_2SO_4/Na_2CO_3$, under ether forming conditions.

Compounds of Formula I, wherein $R_3$ is hydrogen are also useful for preparing compounds wherein $R_3$ is other than hydrogen. These later compounds can also be prepared by art-recognized techniques. For example, compounds of Formula I wherein $R_3$ is OH are reacted with $R_3L$ under substitution conditions, as indicated hereinbelow

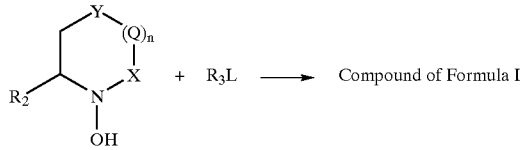

wherein $R_3$ is other than hydrogen

In the above scheme, Q, $R_1$, $R_2$, Y, X, $R_8$, $R_9$, n and $R_3$ are as defined hereinabove and L is a leaving group, such as halo (e.g. chloro or bromo). It is preferable that the reaction is run in an inert polar organic solvent and that the reactants are soluble therein at room temperature. It is also preferred that the product is insoluble in the solvent at room temperature. Examples of the solvent include chloroform, carbon tetrachloride, ethyl ether, dioxane, tetrahydrofuran and methylene dichloride, and the like. The reaction can take place at effective temperatures, which may range from the melting point of the solvent to reflux temperature but it is preferred that the reaction take place at about room temperature or at slightly elevated temperatures up to the reflux temperature of the solvent. It is especially preferred that the reaction take place at room temperature or at slightly elevated temperatures, such as up to 60° C.

The N-oxides can be prepared from the compounds of Formula I having a nitrogen ring heteroatom in the heteroaryl group. These N-oxides are prepared by art-recognized techniques by oxidation thereof, such as with peracid, e.g., peracetic acid or m-chloroperbenzoic acid.

The following examples further illustrate the invention:

EXAMPLE 1

1-Hydroxy-7-aza-benzotriazole

To 13.58 g of 2-nitro-3-methoxypyridine was added 26.4 mL of 95% hydrazine, 10.4 mL of water and 15.3 mL of DMF. The mixture was carefully warmed to about 70° on a hot plate. Spontaneous warming then set in, the temperature rising to about 80° as the solid dissolved. The solution was set aside for 24 hr and then evaporated from a water bath with the aid of a water aspirator to remove excess hydrazine and water. The dark green residue was cooled in an ice bath, diluted with 50 mL of water and acidified to Congo Red with concentrated hydrochloric acid (ca. 17 ml). A yellow-straw-colored solid separated and was filtered and washed with a little cold water to give 6.25 g (52.1%) of HOAt upon recrystallization from 75 mL of water gave 5.46 g (45.5%) of nearly colorless crystals, mp 216°–217° $^1$H NMR ($CDCl_3$-DMSO-$d_6$): δ 7.35 (dd, 1, β-H), 8.3 (dd, 1, γ-H), 8.66 (dd, 1, α-H); $J_{\alpha,\beta}$=4.2 Hz, $J_{\beta,\gamma}$=8.2 Hz, $J_{\alpha,\gamma}$=1.6 Hz. Evaporation of the filtrate gave an additional 0.14 g of the pure hydroxy compound so the total yield was 5.6 g (46.7%).

EXAMPLE 2

[2-(7-Azabenzotriazolyl-1-oxy)-1,1,3,3,-tetramethyluronium hexafluorophosphate]

*N-[(dimethylamino)-1H-1,2,3-triazolo [4,5-b] pyridin-1-yl-methylene]-N-methylmethanaminium hexafluorophosphate*

To a suspension of 0.88 g of 2-chloro-1,1,3,3,-tetramethyluronium hexafluorophosphate in 30 mL of methylene dichloride there was added 0.43 g of HOAt followed by 0.44 mL of $Et_3N$. A clear solution formed and then a granular solid precipitated. After stirring at room temperature for 30 min the solid was filtered, washed twice with 10-mL portions of methylene dichloride and dried in air to give 0.79 g (66.4%) of the uronium salt. Recrystallization by solution in 5 mL of acetonitrile at room temperature, filtration to remove some insoluble crystalline solid and dilution of the filtrate with $CH_2Cl_2$ to a total volume of 25 mL gave 0.51 g (44.6%) of the pure uronium salt as shiny white crystals, darkens at 180° melts with decomposition at 190°–194° (gas); $^1$H NMR (DMSO-$d_6$); δ 3.2 (d, 12, $CH_3N$), 8.0 (dd, 1, β-H), 8.45 (dd, 1, γ-H), 8.9 (dd, 1, α-H); $J_{\alpha,\beta}$=4.4 Hz, $J_{\beta,\gamma}$=8.4 Hz, $J_{\alpha,\delta}$=1.8 Hz.

Anal: Calcl for $C_{10}H_{15}F_6N_6OP$: C, 31.58, A, 3.97, N, 22.09 Found: C, 31.47, H, 3.94, N, 22.12.

EXAMPLE 3

1-Hydroxy-4-aza-benzotriazole

To a suspension of 14.3 g of 2-chloro-3-nitropyridine in 90 mL of anhydrous ethanol was slowly added over 2–3 min with swirling 18 mL of 95% hydrazine. A new solid took the place of the chloro compound as spontaneous warming occurs. After 20 min at room temperature, filtration and washing with ethanol gave 15 g of 2-hydrazino-3-nitropyridine as a straw-yellow solid. To 4 g of the crude hydrazine suspended in 24 mL of anhydrous ethanol was added 16 mL of 95% hydrazine, and the mixture was warmed on a hot plate until the solid dissolved to give a deep red-colored solution and a spontaneous reaction set in with bubbling. The mixture was removed from the source of heat and the reaction allowed to proceed. After 5 min, the mixture was again heated to the boiling point and removed from the hot plate for 5 min. The mixture was treated twice more in this manner after which the deeply-colored solution had become lighter in color (reddish yellow). The solution was evaporated in a warm bath with a water aspirator to a brown oily material which was dissolved in 12 mL of water and acidified (Congo Red) with conc. HCl. Recrystallization from water (Norite) gave 1.10 (31%) of the hydroxytriazole as yellow-colored crystals, mp 203°–211° dec.

EXAMPLE 4

7-Azabenzotriazolyl-1-oxy-trispyrrolidinephosphonium hexafluorophosphate

To a solution of tris-pyrrolidinophosphine (~0.05 moles) dissolved in tetrahydrofuran is added HOAt (~0.05 moles) triethylamine (~0.05 moles) and carbon tetrachloride (~0.1 moles). After stirring at about −30° C., potassium hexafluorophosphate (~0.1 moles) dissolved in water is added to form the above-identified product. Alternatively, an equimolar mixture of trispyrrolidonephosphine oxide and phosphorus oxychloride could be substituted for the trispyrrolidinophosphine and carbon tetrachloride in the above procedure to afford the above-identified compound.

EXAMPLE 5

1-Hydroxy-4-methoxy-7-azabenzotriazole

The above-identified compound is prepared from 3,4-dimethoxy-2-nitropyridine and hydrazine in accordance with the procedure described in Example 1.

Alternatively, 4-methoxy-3-halo-2-nitropyridine, wherein halo is chloro, bromo or fluoro, may be reacted with hydrazine as described above to afford the above-identified compound.

EXAMPLE 6

4-N,N-dimethylamino-1-hydroxy-7-azabenzotriazole

The above-identified compound is prepared by reacting 4-N-N-dimethylamino-3-methoxy-2-nitro pyridine with hydrazine in accordance with the procedure described in Example 1.

Alternatively, 4-N,N-dimethylamino-3-halo-2-nitropyridine is reacted with hydrazine in accordance with the procedure described in Example 1 to afford the above-identified compound.

EXAMPLE 7

1-Hydroxy-6-azabenzotriazole 3-nitro-4-methoxy pyridine is reacted with hydrazine in accordance with the procedure of Example 1 to yield the above-identified compound.

Alternatively, 3-nitro-4-halo pyridine wherein halo is chloro, fluoro or bromo may be reacted with hydrazine to form the above-identified compound.

EXAMPLE 8

1-Hydroxy-5-azabenzotriazole

By reacting either 3-methoxy-4-nitro pyridine or 3-halo-4-nitro pyridine (wherein halo is chloro, bromo or fluoro) with hydrazine in accordance with the procedure of Example 1, the title compound is prepared.

EXAMPLE 9

1-hydroxy-7-aza-1H-indazole

A solution of $Na_2CO_3.10\ H_2O$ (7.3 mmol) in $H_2O$ (10 ml) is emulsified under vigorous stirring at about room temperature or slightly elevated temperature with a solution of 2-nitro-3-methoxypyridine (4.25 mmol) and tetrabutylammonium bromide (10.06 mmol) as phase transfer catalyst in methylene chloride (~20 mL). 2-phenyl-5(4H)-oxazolone (~60 mmol) is added in several portions during one hour. The layers are separated and the aqueous phase is washed with $CH_2Cl_2$. The combined organic solutions are dried with $Na_2SO_4$ and is evaporated under reduced pressure. The residue is chromatographed in silica gel starting with petroleum ether to which methylene chloride is gradually added. After recrystallizing, the complex is placed in refluxing methanol to which a catalytic amount of p-toluene sulfonic acid has been added. The sample is refluxed overnight. After cooling and evaporation of the solvent, the above-identified product is isolated.

EXAMPLE 10

1-Hydroxy-7-azabenzo-1H-imidazole

To a warm solution 2-nitro-3-formamido pyridine in ether is added alc. $(NH_4)_2$ S to afford the above-identified compound.

EXAMPLE 11

1-Hydroxy-1-H-pyrrolo [2,3-b]pyridine

The above product is prepared using the methodology described in Synthesis 1983, 537–38.

A mixture of poly-4-vinylpyridine in tetrahydrofuran is dried by azeotropic distillation. 1-H-pyrrolo [2,3-b]pyridine is introduced, then a solution of dibenzoyl peroxide in tetrahydrofuran is added dropwise. After 24 hours at room temperature, the mixture is heated under reflux for a few hours. The cooled mixture is filtered and the polymer is washed with dichloromethane. The combined organic phases are evaporated under reduced pressure to leave a residue which is diluted with $CH_2Cl_2$ and washed with 10% $Na_2CO_3$ solution. The organic phase is dried with magnesium sulfate and concentrated and recrystallized to give a solid which is dissolved in ether. To the ether solution containing the solid is added potassium methoxide in methanol. The mixture is allowed to be stirred at room temperature for at least 24 hours, and then is concentrated under reduced pressure and the residual white paste is partitioned between water and ether. The organic phase is separated, 5% HCl is added, and the precipitate formed is isolated and washed with ether. The solid is dissolved in 5% sodium carbonate solution and extracted with fresh ether. Drying and concentration of the ether layers gives the above-identified compound.

EXAMPLE 12

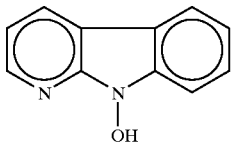

Using the procedure described in Example 11 and using

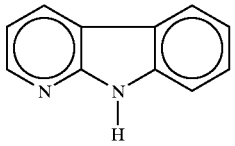

as the starting amine, the above-identified compound can be prepared.

EXAMPLE 13

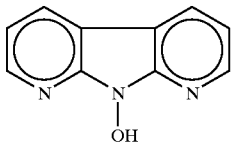

Using the procedure described in Example 11 and using

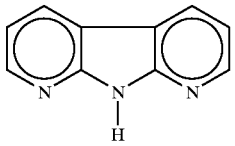

as the amine reactant the above-identified compound is prepared.

EXAMPLE 14

1-hydroxy-2-oxo-2,3-dihydro-7-azaindole

A warm solution of 2-nitro-3-methoxyprydine in tetrahydrofuran was reacted with t-butyl ethyl malonate. The resulting product is next acidified with concentrated hydrochloric acid and then heated and decarboxylated to form ethyl 3-(3-[2-nitropyridyl])propanate. The propanate is reacted with sodium borohydride over palladium on charcoal or ammonium sulfide to afford the above-identified compound.

EXAMPLE 15

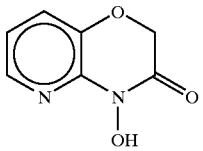

3-hydroxy-2-nitropyridine is treated with potassium hydroxide and the product thereof in turn is reacted with ethyl 2-bromoacetate under Williamson ether conditions to form

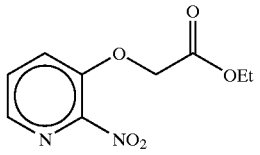

which in turn is reacted with ammonium sulfide or $NaBH_4$/Pd-C to afford the above-identified compound.

EXAMPLE 16

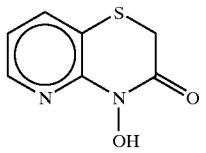

Using the procedure in Example 15 and substituting 3-mercapto-2-nitropyridine for 3-hydroxy-2-nitropyridine, the above compound is prepared.

EXAMPLE 17

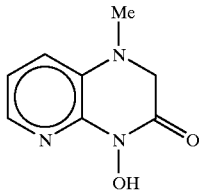

Substituting 3-methylamino-2-nitropyridine for 3-hydroxy-2-nitropyridine, and using the procedure of Example 15, the above-identified compound is prepared.

EXAMPLE 18

1-hydroxy-4-t-butyl-7-azabenzotriazole

The above-identified compound is prepared by reacting 2-nitro-3-methoxy-4-t-butylpyridine with hydrazine in accordance with the procedure described in Example 1.

EXAMPLE 19

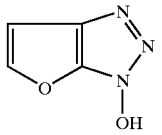

The title compound is prepared by reacting 2-nitro-3-methoxyfuran with hydrazine in accordance with the procedure described in Example 1.

EXAMPLE 20

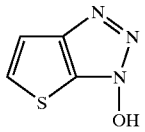

Using the procedure described in Example 18 and replacing the pyridine compound therein with 3-methoxy-2-nitrothiophene, the title compound is prepared.

EXAMPLE 21

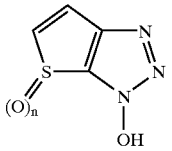

wherein n is 1 or 2.

The above compound is prepared by coupling

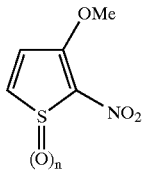

with hydrazine in accordance with the procedure described in Example 1.

EXAMPLE 22

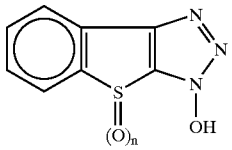

wherein n=0, 1 or 2.

The title compound is prepared by reacting hydrazine with

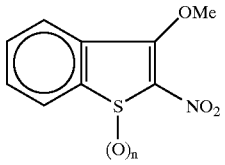

in accordance with the procedure described in Example 1.

EXAMPLE 23

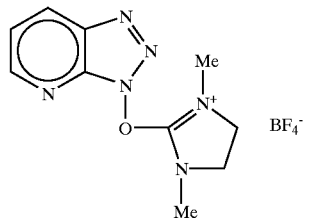

The above-identified compound is prepared by reacting 2-chloro-1,3-dimethylimidazolinium perfluoroborate with HOAt in accordance with the procedure described in Example 2.

EXAMPLE 24

1-phenylsulfonyloxy-7-azabenzotriazole

HOAt is reacted with phenylsulfonyl chloride in accordance with the procedure described in Example 2 to afford the title compound.

EXAMPLE 25 bis-(7-azabenzotraizolyl)carbonate

The title compound is prepared in accordance with the procedure described in Example 2, except that two equivalents of HOAt are reacted with phosgene.

EXAMPLE 26 bis(7-azabenzotriazolyl)oxalate

The title compound is prepared by following the procedure of Example 2, except that oxalyl chloride is used in place of the hexafluorophosphate and two equivalents of HOAt are used.

EXAMPLE 27

N-oxides or S-oxides of Compounds of Examples 1–26

The N-oxides of the compounds of Examples 1–22 are prepared by simple peracid oxidation (e.g., m-chloroperbenzoic acid) of each of said compounds.

The N-oxides of the compounds of Examples 23–26 is prepared by first reacting HOAt with m-chloroperbenzoic acid and then following the procedure in Examples 23–26, using the N-oxide of HOAt instead of HOAt.

The S-oxides are prepared by reacting the thiophene derivatives with peracid oxidation such as m-chloroperbenzoic acid.

EXAMPLE 28

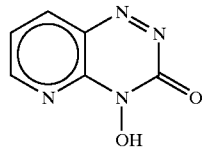

A. Approximately one equivalent of the compound

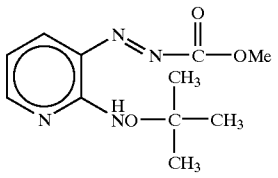

is dissolved in DMF and is reacted slowly with sodium hydride (~1 eq) in DMF. The resulting product, compound 11

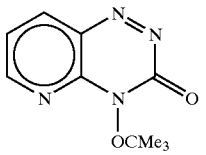

is formed and is isolated from the reaction mixture. Compound 11 is then dissolved in methylene chloride and an excess of trifluoro-acetic acide is added with slight warming to afford the above-identified compound.

B. Alternatively, to a warm solution of compound 12 in ether is

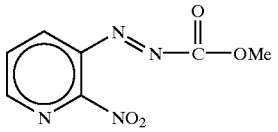

added alcoholic ammonium sulfide to afford the title compound.

EXAMPLE 29

$C_6H_5CH_2OCONHC(CH_3)_2COOAt$ (Z-Aib-OAt). The N-Benzyloxycarbonyl derivative of a-aminoisobutyric acid (Aib; 0.71 g, 3 mmol) was dissolved in 10 mL of dry THF and the solution cooled in an ice bath and treated with 0.411 g (3 mmol) of HOAt followed by 0.618 g of DCC. After 1 h in the ice bath and 2 h at room temperature 20 mL of EtOAc was added and DCU filtered out. The organic filtrate was washed with 5% citric acid, 1M $NaHCO_3$ and saturated NaCl (2×15-mL each), dried ($MgSO_4$), and the solvent removed by Rotovap to give an oil which solidified on the addition of ether. Recrystallization from $CH_2Cl_2$/hexane gave 0.78 g (73%) of the active ester as a white solid, mp 108°–109° C.; IR (KBr) 3328 (NH), 1817 (O-acyl), 1723 (N-acyl), 1700 $cm^{-1}$ (urethane); $^1H$ NMR ($CDCl_3$) δ 1.8 (s, 6H, $CH_3$), 5.22 (s, 2H, $CH_2$), 5.6 (s, 1H, NH), 7.1–7.4 (m, 6H, aryl), 8.3–8.5 (dd, 1H, α-H), 8.6–8.8 (dd, 1H, γ-H).

Anal. Calcd for $C_{17}H_{17}N_5O_4$: C, 57.46; H, 4.79; N, 19.72. Found: C, 57.84; H, 4.94; N, 19.46.

Z-Aib-OAt was reacted with p-chloroaniline under amide forming conditions to give the amide, Z-Aib-$NHC_6H_4Cl$-p.

EXAMPLE 30

Z-Phe-OAt

Starting from Z-phenylalanine the preparation followed that which was given for Z-Aib-OAt, the ester being obtained in 76.5% yield as a white solid, mp 130°–132° C.; IR (KBr) 3328 (NH), 1823 (O-acyl), 1721 (N-acyl), 1700 $cm^{-1}$ (urethane); $^1H$ NMR ($CDCl_3$) δ 3.5 (d, 2H, $CH_2$), 5.1–5.2 (m, 3H, CH, $CH_2$), 7.2–7.4 (m, 11H, aryl and β-H), 8.4 (d, 1H, α-H), 8.9 (d, 1H, γH).

Anal. Calcd for $C_{22}H_{19}N_5O_4$: C, 63.31; H, 4.56. Found: C, 63.59; H, 4.78.

EXAMPLE 31

Z-Phg-OAt

Starting from Z-α-phenylglycine the preparation followed that which was given for Z-Aib-OAt, the active ester being obtained in 84.2% yield as a foamy solid, mp 48°–51° C.; IR (KBr) 3318 (NH), 1823 (O-acyl), 1718 (N-acyl), 1700 $cm^{-1}$ (urethane); $^1H$ NMR ($CDCl_3$) δ 5.18–5.3 (m, 3H, CH, $CH_2$), 5.9 (d, 1H, NH), 7.1–7.6 (m, 11H, aryl and β-H), 8.4–8.5 (dd, 1H, α-H), 8.6–8.8 (dd, 1H, γH).

EXAMPLE 32

Comparison of Reactivity of P-Benzoyl Derivatives of HOBt, 7-HOAr and 4-HOAt The three O-benzoyl derivatives were obtained by reaction of 1 eq of HOXt wherein X is A or B, with 1 eq of benzoyl chloride and 1 eq of $NEt_3$ (e.g., 68 mg 4-HOAt, 70 mg $C_6H_5COCl$, 50.5 mg $NEt_3$ in 5 mL of $CH_2$—$Cl_2$). After a quick water wash, evaporation gave a solid which was recrystallized from toluene/hexane to give the active esters as white crystals. To 12.9 mg of t-octylamine in 0.8 g of $CDCl_3$ was added in three separate vessels 12 mg of the three O-benzoyl esters. In the case of O-benzoyl-7-HOAt and O-benzoyl-4-HOAt, acylation was complete within two minutes whereas for 0-benzoyl-HOBt reaction required about 1 hour. Further experiments using a less reactive nucleophile (such as p-chloroaniline), in accordance with the coupling procedure described in Example 33 showed that 7-aza esters of this type were about twice as reactive as the 4-aza analogs. Both of these esters exceeded the reactivity of the HOBt ester by factors of 10–20.

EXAMPLE 33

General Procedure for Test Couplings. To a solution of 0.37 mmols of a protected amino acid, 0.33 mmols of HOBt or compounds of Formula I e.g., HOAt, or other additive, 0.33 mmols of an amino acid ester (or 0.33 mmols of the corresponding hydrochloride plus an equivalent amount of a tertiary amine) in 1 mL of DMF cooled in an ice bath was added 0.37 mmols of DCC or EDC or other condensing agents. For reactions involving HOAt the disappearance of the yellow color signaled the end of the coupling process and work up followed soon thereafter. For other additives workup times were arbitrary. Work up consisted of dilution with 10 mL of $CH_2Cl_2$ followed by 200 mL of water, collection of the organic layer and extraction with four or five additional 8- to 10-mL portions of $CH_2Cl_2$. The combined extracts were washed with two 10-mL portions of 10% HCl, one 10-mL portion of water and two 10-mL portions of 0.5M $NaHCO_3$. Drying ($MgSO_4$) and evaporation of solvent gave the protected peptide ester which was examined by $^1$NMR for the presence of diastereomeric contamination. The results of some couplings are depicted in Table 1.

EXAMPLE 34

Z-Phe-OAt is reacted with valine methyl ester in DMF in accordance with the procedure described in Example 33 to form Z-Phe-Val.

TABLE 1

Comparison of HOAt and HOBt In the Coupling[a,b] of PG-AA[1]-OH + H-AA[2]-OMe.HCl

| Run | PG | AA[1] | AA[2] | Conditions[c] | Yield (%) | DL-(%) |
|---|---|---|---|---|---|---|
| 1 | Z | Phg | Val | HOAt, PS (1 eq), EDC, 9 h | 90.6 | <1 |
| 2 | Z | Phg | Val | HOBt, PS (1 eq), EDC, 9 h | 94.0 | 3.7 |
| 3 | Z | D-Phg | Val | HOAt, PS (1 eq), EDC, 6 h | 70.0 | <1 |
| 4 | Z | Phg | Val | HATU, DIEA (2 eqs), 7 h | 62.8 | <1 |
| 5 | Z | Phg | Val | HBTU, DIEA (2 eqs), 7 h | 56.5 | 3.8 |
| 6 | Z | Phe-Val | Ala | HOAt, NMM (1 eq), EDC, 1¼ h | 72.0 | <1 |
| 7 | Z | Phe-Val | Ala | HOBt, NMM (1 eq), EDC, 2¼ h | 75.0 | 4.1 |
| 8 | Z | Phe-Val | Ala | HATU, DIEA (2 eqs), 3½ h | 88.0 | <1 |
| 9 | Z | Phe-Val | Ala | HBTU, DIEA (2 eqs), 4 h | 72.5 | 3.6 |
| 10 | Bz | Val | Val | HOAt, NMM (1 eq), EDC, 20 h | 72.0 | 28.1 |
| 11 | Bz | Val | Val | HOBt, NMM (1 eq), EDC, 20 h | 71.9 | 45.4 |
| 12 | Bz | Val | Val | DCC, 24 h | 70.0 | 61.5 |
| 13 | Bz | Val | Val | HOAt, DCC, 24 h | 87.9 | 14.4 |
| 14 | Bz | Val | Val | HOBt, DCC, 24 h | 85.0 | 41.9 |
| 15 | Bz | Val | Val | HOAt, DCC, DCM solvent, 24 h | 96.7 | <1 |
| 16 | Bz | Val | Val | HATU, NMM (2 eqs), 3 h | 89.8 | 28.3 |
| 17 | Bz | Val | Val | HBTU, NMM (2 eqs), 3½ h | 88.0 | 46.8 |

TABLE 1-continued

| Comparison of HOAt and HOBt In the Coupling[a,b] of PG-AA[1]-OH + H-AA[2]-OMe.HCl | | | | | | |
|---|---|---|---|---|---|---|
| Run | PG | AA[1] | AA[2] | Conditions[c] | Yield (%) | DL-(%) |
| 18 | BOC | Aib | Aib | HOAt, NMM (1 eq), EDC, 24 h | 99.3 | — |
| 19 | BOC | Aib | Aib | HOBt, NMM (1 eq), EDC, 24 h | 65.0 | — |

[a]Test couplings were carried out by preparing a solution of 0.37 mmol of a protected amino or dipeptide acid, 0.33 mmol of HOAt or HOBt, 0.33 mmol of an amino acid ester (or its hydrochloride plus an equivalent amount of a tertiary amine) in 1 mL of DMF. The mixture was cooled in an ice bath and treated with 0.37 mmol of DCC or EDC. For reactions involving uroniuim salts 0.74 mmol of a tertiary amine was substituted for the HOAt or HOBt. For HOAt reactions in the absence of excess amino component or tertiary base disappearance of the yellow color signaled completion of the coupling process and work-up proceeded soon thereafter. In other cases work-up times were arbitrary. Generally stirring was continued in the ice bath for 1½–2 h and then at room temperature for the times indicated. Dilution with 15 mL of $CH_2Cl_2$ and 200 mL of water was followed by extraction with 4–5 10-mL portions of $CH_2Cl_2$ and washing in order with 10-mL portions of 10% HCl (twice), $H_2O$ (once) and 0.5 M $NaHCO_3$ (twice). Drying and removal of solvent gave the crude peptide which was examined by $^1H$ NMR for the presence of diastereomeric contamination (OMe and/or $Me_2CH$—).
[b]Abbreviations: PG = protecting group, $AA_1$, $AA_2$ = amino acid or dipeptide fragment, PS = proton sponge (1,8-bis(N,N-dimethylamino)naphthalene), EDC = N-ethyl-N'-(3-dimethylamino-propyl)-carbodiimide hydrochloride, DIEA = diisopropylethylamine, NMM = N-methyl-morpholine, DCC = dicyclohexylcarbodiimide. DCM = dichloromethane, Z = benzyloxycarbonyl, Bz = benzoyl, BOC = t-butyloxycarbonyl.
[c]All reactions were carried out in DMF except where indicated.

Table 1 illustrates the effectiveness of the compounds of the present invention in promoting peptide coupling. This is demonstrated using a representative example, such as HOAt. Further, the table illustrates the effectiveness of compounds of the present invention, such as HOAt, in reducing racemization.

One model system that was used involved coupling of an urethane protective derivative of the sensitive non-proteinogenic amino acid α-phenylglycine and comparing the amount of racemization when HOBT and an exemplary compound of the present invention, e.g., HOAt, were used as the additive. For example, upon treatment of the benzyloxycarbonyl derivative with valine methyl ester hydrochloride in the presence of HOBt and an equivalent of proton sponge or with HBTU and two equivalents of DIEA, 3.7–3.8% of the DL-diastereomer was formed (runs 2 and 5). This was reduced to less than 1% by substitution of HOAt for HOBt in these reactions (runs 1 and 4).

A second example, even more promising in view of its relevance to segment coupling, involved reaction of Z-Phe-Val-OH with alanine methyl ester. With this system HOBt- or HBTU-coupling (runs 7 and 9) in the presence of NMM or DIEA gave 3.6–4.1% of the LDL-isomer. Again in this case, the use of compounds of the present invention, e.g., HOAt or HATU lowers the extent of racemization to less than 1% (runs 6 and 8). Finally the highly sensitive coupling of benzoylvaline with valine methyl ester shows that HOAt reduces racemization to about one fourth or one half the level found for comparable HOBt reactions (runs 10–17). For this system, even with HOAt, only in a non-polar solvent such as dichloromethane was it possible to effect coupling without detectable racemization.

An example of the accelerated reactivity in the presence of compounds of the present invention is illustrated in the following example:

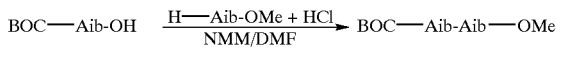

This example involves the coupling of the hindered amino acid α-amino isobutyric acid (Aib). In the presence of HOBt, this reaction is incomplete after 24 hours (25–35% HOBt ester remaining unreacted) whereas complete coupling is observed with HOAt.

The compounds of the present invention are also useful in promoting the coupling of an amine with a carboxylic acid or acylating derivative thereof. For example, the reaction of a hindered secondary amine 23 with BOC-Pro-OH is over within 3½ hr in the presence of HOAt, whereas it is still incomplete after 24 hours

23

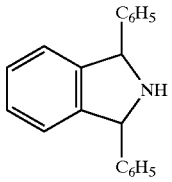

24

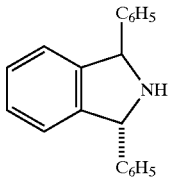

with HOBt. Similarly benzoylation of the even more hindered trans-amine 24 via EDC along with either HOBt or HOAt requires about 48 hours in the case of HOBt and only 5 hours for HOAt.

Ester-, as well as amide-bond formation can be achieved with these reagents. In the present study it was found that formation of the methyl ester of the dipeptide FMOC-Phg-Phe-OH in the presence of HOBt and a catalytic amount of proton sponge occurred with contamination by 20.5% of the D, L-form whereas with HOAt under the same conditions, racemization was not eliminated although it could be reduced to 7.5%. On the other hand it was found that with HOAt no base was required and in that case no significant racemization occurred. A parallel reaction with HOBt alone gave only a trace of the ester under the same conditions.

As indicated above, compounds of the present invention, e.g. HOAt, are also unique in exhibiting the effect of a built-in indicator which, under appropriate conditions, signals completion of the coupling reaction. For example, the anion of HOAt

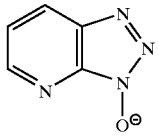

is yellow. In the presence of an amino acid or peptide ester, HOAt is converted to its highly colored yellow anion. As coupling proceeds, the color fades and then disappears completely. For couplings between unhindered amino acid residues, this happens within 15–20 min in DMF solution. On the other hand, current recipes for the use of HOBt as an additive often involve reaction periods of 10–24 hours.

It should be noted that the maximum neighboring group effect (reactivity acceleration and racemization reduction) is observed when the heteroatom in the adjacent fused ring is in the neighboring group position relative to the (N—O) bond. For example, the neighboring group effect is greater in HOAt, i.e.,

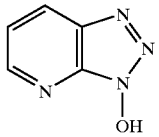

than in 1-hydroxy-4-azabenzotriazole, i.e.,

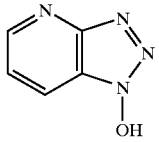

However, in cases like the latter, reactivity is still accelerated, but no racemization reduction is observed. But, there are times when only acceleration is needed, such as in step-wise solid phase synthesis, wherein there is no fear of racemization. Compounds wherein the heteroatom is not on the neighboring group relative to the N—O bond satisfy those needs.

The above preferred embodiments and examples are given to illustrate the scope and spirit of the present invention. These embodiments and examples will make apparent to those skilled in the art other embodiments and examples. These other embodiments are also examples within the contemplation of the present invention. Therefore, the presentation invention should be limited only by the appended claims.

What is claimed:

1. A process for preparing a peptide bond comprising reacting an amino compound with a carboxylic acid in the presence of an effective amount of a compound having the formula:

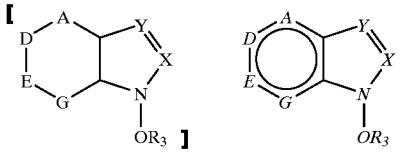

or N-oxides thereof a salts thereof;

wherein said amino compound is an amino acid or peptide and said carboxylic acid is a N-terminal amino protected amino acid or a N-terminal amino protected peptide;

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently hydrogen lower alkyl or an electron-donating group;

X is $CR_7$ or N;

Y is N or $CR_5$;

$R_7$ and $R_5$ are independently hydrogen or lower alkyl;

$R_3$ is $SO_2R_{14}$ or a positively charged electron-withdrawing group, *of the formula* $P^{\oplus}(NR_{12}R_{13})_3$;

*each* $R_{12}$ *and* $R_{13}$ *are independently hydrogen, lower alkyl or lower alkoxy lower alkyl or* $R_{12}$ *and* $R_{13}$ *taken together with the nitrogen atom to which they are attached form a 5- or 6- membered heterocylic ring containing up to a total of 5 ring carbon atoms;* and $R_{14}$ is lower alkyl, aryl or aryl loweralkyl.

2. A process for preparing a peptide bond comprising reacting an amino compound and a carboxylic acid in the presence of a dehydrating reagent and an effective amount of a compound, said compound having the formula:

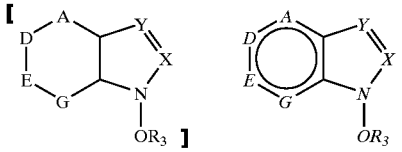

or N-oxides thereof or salts thereof;

wherein said amino compound is an amino acid or peptide and said carboxylic acid is a N-terminal amino protected amino acid or a N-terminal amino protected peptide;

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently hydrogen, lower alkyl or an electron-donating group;

X is $CR_7$ N;

Y is N or $CR_5$;

$R_7$ and $R_5$ are independently hydrogen or lower alkyl;

and $R_3$ is hydrogen.

3. A process for preparing a peptide bond comprising reacting an amino compound and an acylating derivative of a carboxylic acid in the presence of an effective amount of a compound, said compound having the formula:

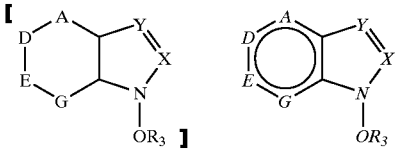

or N-oxides thereof or salts thereof;

wherein said amino compound is an amino acid or peptide and said carboxylic acid is a N-terminal amino protected amino acid or a N-terminal amino protected peptide;

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently hydrogen, lower alkyl or an electron-donating group;

X is $CR_7$ or N;

Y is N or $CR_5$;

$R_7$ and [$R_8$ ] $R_5$ are independently hydrogen or lower alkyl;

and $R_3$ is hydrogen.

4. A process for preparing a peptide bond comprising reacting an amino compound selected from the group consisting of an amino acid and a peptide with an effective amount of a compound having the formula:

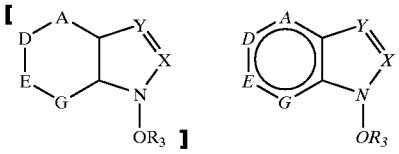

wherein or N-oxides thereof or salts thereof;

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently hydrogen, lower alkyl or an electron-donating group;

X is $CR_7$ or N;

Y is N or $CR_5$;

$R_7$ and $R_5$ are independently hydrogen or lower alkyl;

$R_3$ is $BLK_1$–$AA_1$;

$BLK_1$ is an amino acid protecting group; and $AA_1$ is an amino acid or peptide less a hydrogen on the N-terminus and an OH on the C-terminus.

5. The process according to any of claim 1–4 wherein A or G is N.

6. The process according to any one of claims 1–4 wherein Y is CH or N and X is CH or N.

7. The process according to any one of claim 1–4 wherein the electron-donating group is amino, lower alkylamino, diloweralkylamino, hydroxy, lower alkoxy, lower aralkoxy, halo, aryl, mercapto or lower alkylthio.

8. The process according to claim 7 wherein the electron-donating group is lower dialkylamino or lower alkoxy.

9. The process according to claim 8 wherein the electron-donating group is OMe or $Me_2N$.

10. The process according to claim 2 wherein the *dehydrating* agent is DCC or EDC.

11. The process according to claim 3 in which the acylating derivative of the carboxylic acid is

BLK-AA-M wherein BLK is an amino protecting group;

AA is an amino acid;

M is halo or phenoxy ester wherein the phenyl group is of the formula:

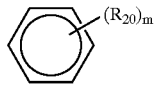

wherein $R_{20}$ is independently halo or an electron-withdrawing group and m is 1–5.

12. The process according to claim 11 wherein BLK is FMOC, BOC, TEOC, Aoc, Adoc, Bpoc, Azoc, Ddz, Proc, Foc, Moz, Nps, Dts, Cbz, Bspoc, Bsmoc, [Nps,] formyl, acetyl, trifluoroacetyl, CLIMOC or BIMOC.

13. The process according to claim 12 wherein BLK is Cbz, Bspoc, Bsmoc, BOC or FMOC.

14. The process according to claim 11 wherein the electron-withdrawing group is nitro or cyano.

[15. The process according to claim 1 wherein the positively charged electron-withdrawing group is

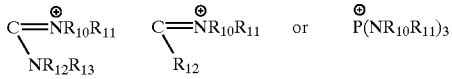

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached from a 5 or 6 membered nitrogen-containing heterocyclic ring containing up to a total of 5 carbon ring atoms.]

16. The process according to claim [15] *1* wherein [$R_{10}$, $R_{11}$,] $R_{12}$ and $R_{13}$ are independently hydrogen, lower alkyl or lower alkoxy lower alkyl.

17. The process according to claim 16 wherein [$R_{10}$, $R_{11}$,] $R_{12}$ and $R_{13}$ are independently lower alkyl.

18. The process according to claim 17 wherein [$R_{10}$, $R_{11}$,] $R_{12}$ and $R_{13}$ are methyl.

[19. The process according to claim 15 wherein the positively charged electron-withdrawing group is

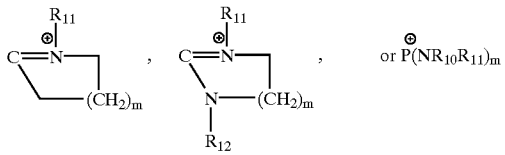

wherein $R_{10}$, $R_{11}$, $R_{12}$ are independently hydrogen, lower alkyl or loweralkoxy lower alkyl and m is 0 or 1.]

20. The process according to claim [19] *1* wherein [$R_{11}$ and $R_{12}$ are the same and $R_{10}$ and $R_{11}$ ] $R_{12}$ *and* $R_{13}$ are the same.

21. The process according to claim 1 wherein $R_3$ is

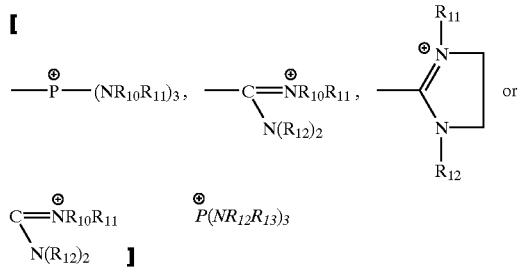

wherein

[$R_{10}$, $R_{11}$ and] $R_{12}$ *and* $R_{13}$ *each* are independently hydrogen, methyl, ethyl, propyl, butyl, pentyl, or $CH_2CH_2OCH_2CH_3$.

22. The process according to claim 21 wherein [$R_{10}$, $R_{11}$ and $R_{12}$ ] $R_{12}$ *and* $R_{13}$ are the same.

23. The process according to claim 1 wherein $R_3$ is

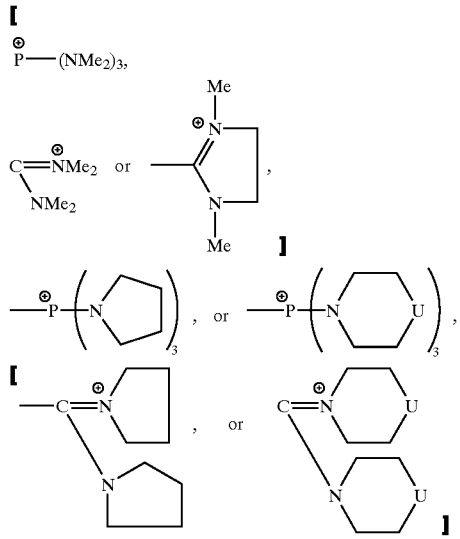

wherein

U is N-ALK, $CH_2$ or O; and

ALK is lower alklyl or hydrogen.

24. The process according to claim 23 wherein U is $CH_2$.

25. The process according to claim 1 wherein the compound has the formula:

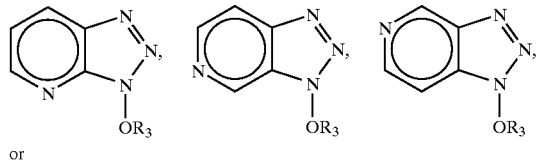

or

-continued

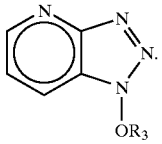

26. The process according to claim 2 or claim 3 wherein the compound has the formula:

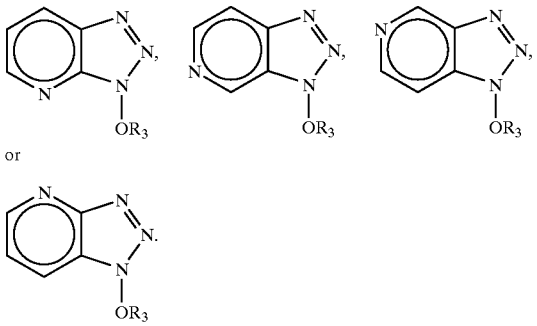

27. The process according to claim 4 wherein the compound has the formula:

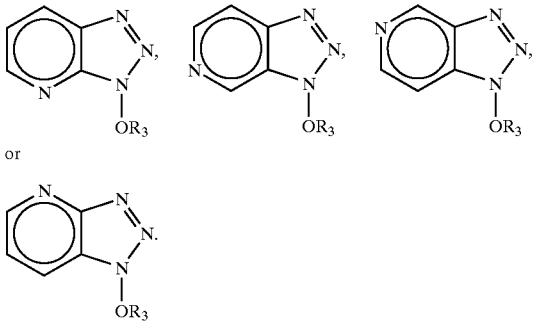

28. The process according to claim 27 wherein $R_3$ is $BLK_1$–$AA_1$ wherein $BLK_1$ is FMOC, BOC, TEOC, Aoc, Adoc, Bpoc, Azoc, Ddz, Poc, Foc, Moz, Nps, Nts, Cbz, Bspoc, Bsmoc, [Nps,] formyl, acetyl, trifluoroacetyl, CLIMOC or BIMOC.

29. The process according to claim 28 wherein $R_3$ is $BLK_1$–$AA_1$, wherein $BLK_1$ is Cbz, Bspoc, Bsmoc, BOC or FMOC.

30. The process according to claim 25 wherein $R_3$ is a positively charged electron-withdrawing group.

[31. The process according to claim 30 wherein $R_3$ is

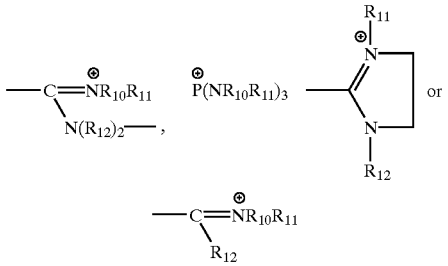

wherein $R_{10}$, $R_{11}$, and $R_{12}$ are independently hydrogen, lower alkyl or lower alkoxy lower alkyl.]

[32. The process according to claim 31 wherein $R_{10}$, $R_{11}$, and $R_{12}$ are independently hydrogen, methyl, ethyl, propyl, butyl, pentyl or $CH_2CH_2OCH_2CH_3$.]

[33. The process according to claim 31 or 32 wherein $R_{10}$, $R_{11}$ and $R_{12}$ are the same.]

[34. The process according to claim 25 wherein $R_3$ is

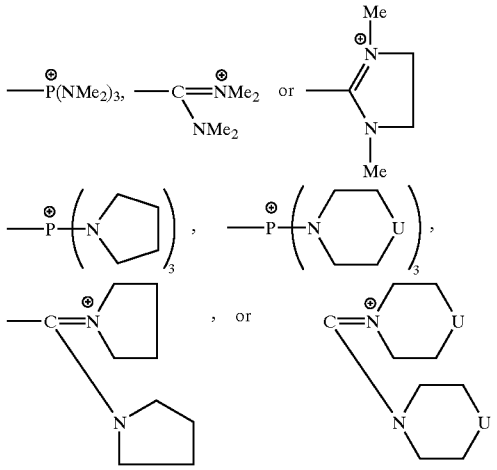

wherein

U is N-ALK, $CH_2$ or O, and ALK is lower alkyl or hydrogen.]

35. The process according to claim [34] *23* wherein U is $CH_2$ or NH.

36. The process for preparing a peptide bond comprising reacting an amino compound with a carboxylic acid in the presence of an effective amount of a compound having the formula:

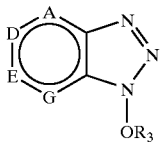

or N-oxides thereof or salts thereof wherein said amino compound is an amino acid or peptide and said carboxylic acid is a N-terminal amino protected amino acid or a N-terminal amino protected peptide;

D is $CR_{16}$ or N;

E is $CR_{17}$ or N;

A is $CR_{15}$ or N;

G is [$CR_{15}$ ] $CR_{18}$ or N;

and one or two of A, D, E, G is N;

$R_{15}$, $R_{16}$, $R_{17}$ and $R_{18}$ are independently hydrogen, lower alkyl or an electron-donating group;

$R_3$ is $SO_2R_{14}$ or a positively charged electron-withdrawing group *having the formula* $P^{\oplus}(NR_{12}R_{13})_3$;

*each* $R_{12}$ *and* $R_{13}$ *are independently hydrogen, lower alkyl or lower alkoxy lower alkyl or* $R_{12}$ *and* $R_{13}$ *taken together with the nitrogen atom to which they are attached form a 5- or 6- membered heterocyclic ring containing up to a total of 5 ring carbon atoms*;

and $R_{14}$ is lower alkyl, aryl, or aryl lower alkyl.

37. A process for preparing a peptide bond comprising reacting an amino compound with a carboxylic acid in the presence of a dehydrating reagent and an effective amount of a compound having the formula

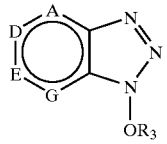

or N-oxides thereof or salts thereof; wherein said amino compound is an amino acid or peptide and said carboxylic acid is a N-terminal amino protected amino acid or a N-terminal amino protected peptide, D is $CR_{16}$ or N;

E is $CR_{17}$ or N;

A is [$CR_{18}$ ] $CR_{15}$ or N;

G is $CR_{18}$ or N;

and one or two of A, D, E, G is N;

$R_{15}$, $R_{16}$, $R_{17}$ and $R_{18}$ are independently hydrogen, lower alkyl or an electron-donating group;

and $R_3$ is hydrogen.

38. A process for preparing a peptide bond comprising reacting an amino compound with an acrylating derivative of a carboxylic acid in the presence of an effective amount of a compound having the formula:

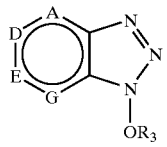

or N-oxides thereof or salts thereof; wherein said amino compound is an amino acid or peptide and said carboxylic acid is a N-terminal amino protected amino acid or a N-terminal amino protected peptide;

D is $CR_{16}$ or N;

E is $CR_{17}$ or N;

A is $CR_{15}$ or N;

G is $CR_{18}$ or N;

and one or two of A, D, E, G is N;

$R_{15}$, $R_{16}$, $R_{17}$ and $R_{18}$ are independently hydrogen, lower alkyl or an electron-donating group;

and $R_3$ is hydrogen.

39. A process for preparing a peptide bond comprising reacting an amino compound selected from the group consisting of an amino acid and a peptide with an effective amount of a compound having the formula:

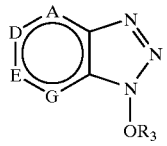

or N-oxides thereof or salts thereof wherein

D is $CR_{16}$ or N;

E is $CR_{17}$ or N;

A is $CR_{15}$ or N;

G is $CR_{18}$ or N;

and one or two of A, D, E, G is N;

$R_{15}$, $R_{16}$, $R_{17}$ and $R_{18}$ are independently hydrogen, lower alkyl or an electron-donating group;

$R_3$ is $BLK_1$–$AA_1$;

$BLK_1$ is an amino acid protecting group; and $AA_1$ is an amino acid or peptide less a hydrogen on the N-terminus and OH on the C-terminus.

40. The process according to any of claims 36–39 wherein two of A, D, E and G are N.

41. The process according to any one of claims 36–39 wherein the electron-donating group is amino, lower alkylamino, diloweralkylamino, hydroxy, lower alkoxy, lower alkoxy, halo, aryl, mercapto or lower alkylthio.

42. The process according to claim 41 wherein the electron-donating group is lower dialkylamino or lower alkoxy.

43. The process according to claim 36 wherein $R_3$ is a positively charged electron-withdrawing group.

[44. The process according to claim 43 wherein $R_3$ is

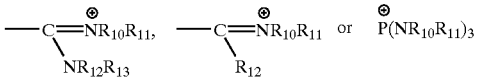

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_3$ taken together with the nitrogen atoms to which they are attached form a 5 or 6 membered nitrogen-containing heterocyclic ring containing up to a total of 5 carbon ring atoms.]

45. The process according to claim 36 wherein [$R_3$ is

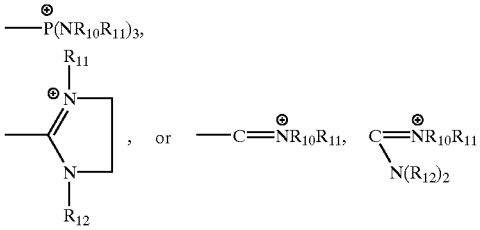

wherein $R_{10}$, $R_{11}$, $R_{12}$ ] *$R_{12}$ and $R_{13}$ each* are independently hydrogen, lower alkyl or lower alkoxy lower alkyl.

46. The process according to claim 44 or 45 wherein [$R_{10}$, $R_{11}$, and $R_{12}$] *$R_{12}$ and $R_{13}$ each* are independently hydrogen, methyl, ethyl, propyl, butyl, pentyl or $CH_2CH_2OCH_2CH_3$.

47. The process according to claim [46] *45* wherein [$R_{10}$, $R_{11}$ and $R_{12}$] *$R_{12}$ and $R_{13}$* are the same.

48. The process according to claim 36 wherein $R_3$ is

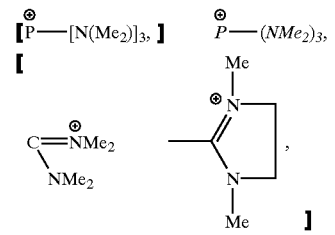

-continued

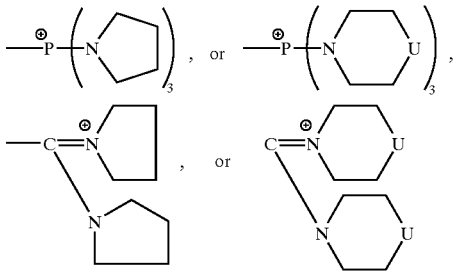

wherein

U is N-ALK, $CH_2$ or O and ALK is lower alkyl or hydrogen.

49. The process according to claim 48 wherein U is $CH_2$ or NH.

50. The process according to claim 1 wherein the compound has the formula

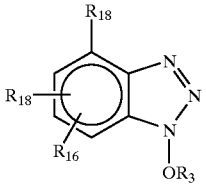

wherein one of $R_{16}$, $R_{17}$ and $R_{18}$ is hydrogen, lower alkyl or an electron-donating group and the others are hydrogen.

$R_3$ is [a] *the* positively charged electron-withdrawing group or $SO_2R_{14}$; and $R_{14}$ is lower alkyl, aryl or lower arylakyl.

51. The process according to claim 2, wherein the compound has the formula:

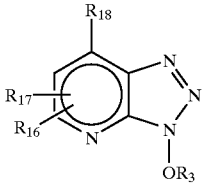

wherein one of $R_{16}$, $R_{17}$ and $R_{18}$ is hydrogen, lower alkyl or an electron-donating group and the others are hydrogen, and $R_3$ is H.

52. The process according to claim 3, wherein the compound has the formula:

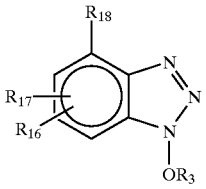

wherein one of $R_{16}$, $R_{17}$ and $R_{18}$ is hydrogen, lower alkyl or an electron donating group and the others are hydrogen and $R_3$ is H.

53. The processing according to claim 4 wherein the compound has the formula:

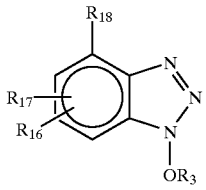

wherein one of $R_{16}$, $R_{17}$ and $R_{18}$ is hydrogen, lower alkyl or an electron-donating group and the others are hydrogen, and $R_3$ is $BLK_1$–$AA_1$.

54. The process according to any of claims 50–53 wherein $R_{16}$ is an electron-donating group.

55. The process according to claim 54 wherein $R_{16}$ is lower alkylamino, diloweralkylamino, amino, hydroxy, lower alkoxy, loweraralkoxy, aryloxy, aryl, lower aralkyl, mercapto or loweralkylthio.

56. The process according to claim 55 wherein $R_{16}$ is diloweralkylamino or lower alkoxy.

57. The process according to claim 56 wherein $R_{16}$ is $OCH_3$ or $Me_2N$.

58. The process according to any one of claims 50–53 wherein the compound has the formula:

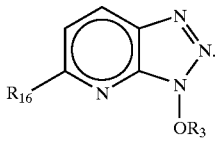

59. The process according to any one of claims 50–53 wherein the compound has the formula:

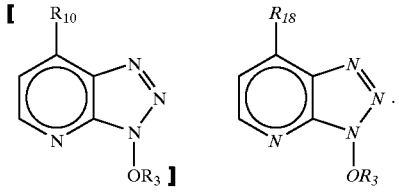

60. The process according to claim 50 wherein [$R_3$ is

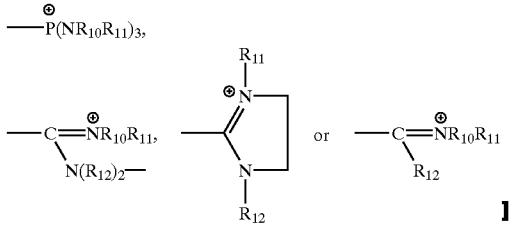

wherein

[$R_{10}$, $R_{11}$, $R_{12}$] $R_{12}$ and $R_{13}$ *each* are independently hydrogen, lower alkyl or lower alkoxy lower alkyl.

61. The process according to claim 60 wherein [$R_{10}$, $R_{11}$, and $R_{12}$] $R_{12}$ *and* $R_{13}$ *each* are independently hydrogen, methyl, ethyl, propyl, butyl, pentyl or $CH_2CH_2OCH_2CH_3$.

62. The process according to claim 60 or 61 wherein [$R_{10}$, $R_{11}$ and $R_{12}$] $R_{12}$ *and* $R_{13}$ are the same.

63. The process according to claim 50 wherein $R_3$ is

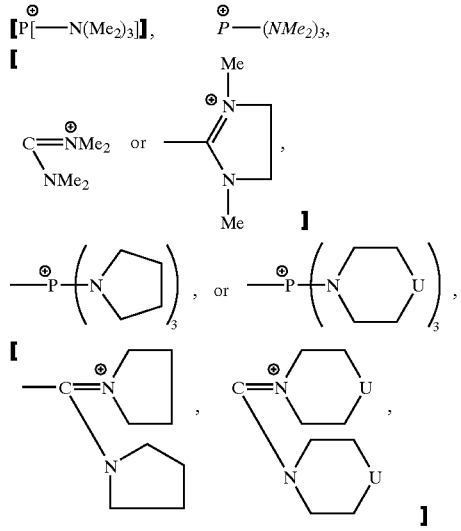

wherein

U is N-ALK, $CH_2$, or O, and ALK is lower alkyl or hydrogen.

64. The process according to claim 2 or claim 3 wherein the compound has the formula:

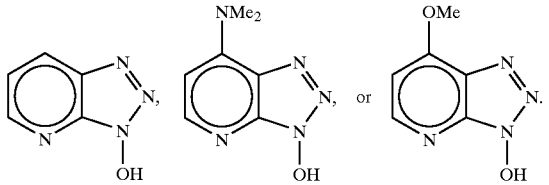

65. The process according to claim 1 wherein the compound *is a salt and the cation* has the formula:

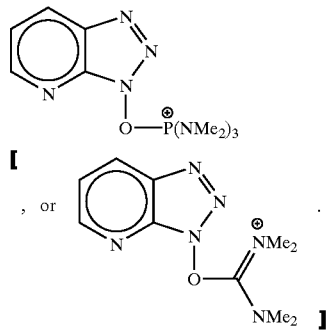

66. The process according to claim 2 or claim 3 wherein the compound has the formula:

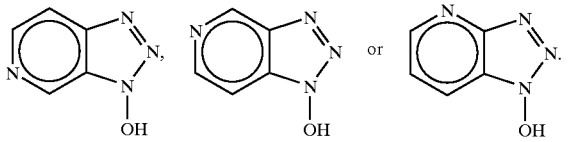

67. The process according to claim 1 wherein the compound has the formula:

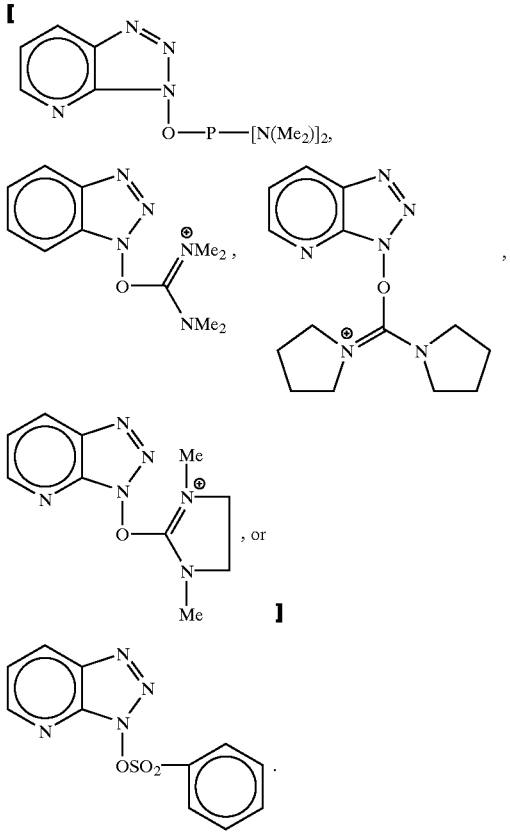

68. The process according to claim [1] *2 or 3* wherein the compound has the formula:

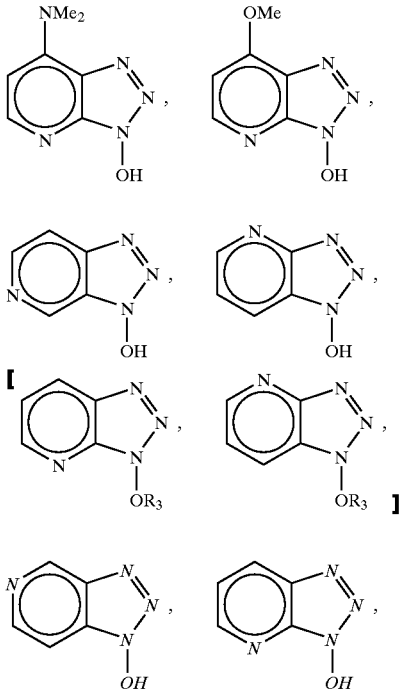

-continued

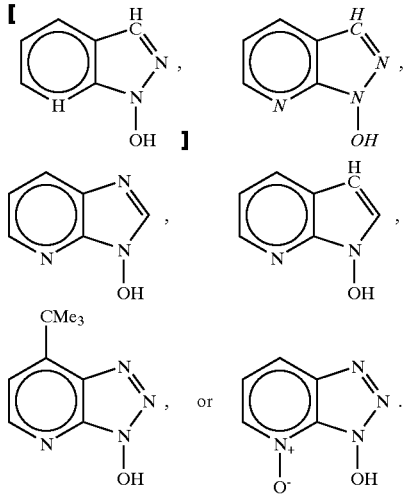

69. The process according to claim 1 [or 3] where the compound is of the formula:

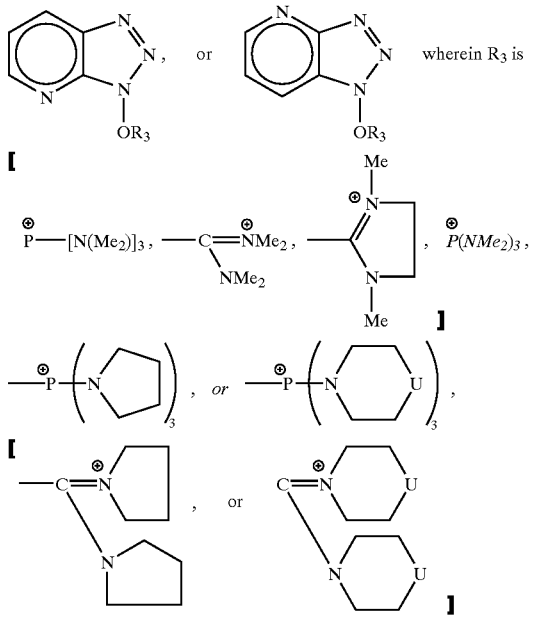

wherein

U is $CH_2$, O or N-ALK and ALK is H or lower alkyl.

70. The process according to claim 69 wherein U is $CH_2$.

71. The process for forming an amide comprising reacting an organic amine and a carboxylic acid in the presence of an effective amount of a compound having the formula:

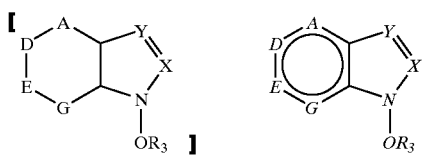

or N-oxides thereof or salts thereof;

wherein

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently hydrogen, lower alkyl or an electron-donating group;

X is $CR_7$ or N;

Y is N or $CR_5$;

$R_7$ and $R_5$ are independently or lower alkyl;

$R_3$ is $SO_2R_{14}$ or a positively charged electron-withdrawing group *of the formula* $P^{\oplus}(NR_{12}R_{13})_3$;

*each* $R_{12}$ *and* $R_{13}$ *are independently hydrogen, lower alkyl or lower alkoxy lower alkyl or* $R_{12}$ *and* $R_{13}$ *taken together with the nitrogen atom to which they are attached form a 5- or 6- membered heterocyclic ring containing up to a total of 5 ring carbon atoms*; and and $R_{14}$ is lower alkyl, aryl or aryl loweralkyl.

72. A process for forming an amide comprising reacting an organic amine with a carboxylic acid in the presence of a dehydrating reagent with an effective amount of a compound having the formula:

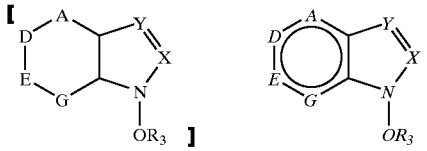

or N-oxides thereof or salts thereof;

wherein

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently, hydrogen, lower alkyl or an electron-donating group;

X is $CR_7$ or N;

Y is N or $CR_5$;

$R_7$ and $R_5$ are independently hydrogen or lower alkyl; and $R_3$ is hydrogen.

73. The process according to claim 71 or 72 wherein A or G is N.

74. The process according to claim 71 or 72 wherein Y is CH or N and X is CH or N.

75. The process according to claim 71 or 72 wherein the electron-donating group is amino, lower alkylamino, dilower-alkylamino, hydroxy, lower alkoxy, lower aralkoxy, halo, aryl, mercapto or lower alkylthio.

76. The process according to claim 71 or 72 wherein the electron-donating group is lower dialkyamino or lower alkoxy.

77. The process according to claim 76 wherein the electron-donating group is OMe or $Me_2N$.

[78. The process according to claim 71 wherein the positively charged electron-withdrawing group is

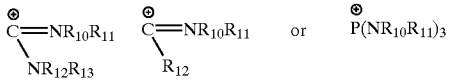

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached from a 5 or 6 membered nitrogen-containing heterocyclic ring containing up to a total of 5 carbon ring atoms.]

79. The process according to claim [78] *71* wherein [$R_{10}$, $R_{11}$,] $R_{12}$ and $R_{13}$ are *each* independently hydrogen, lower alkyl or lower alkoxy lower alkyl.

80. The process according to claim 79 wherein [$R_{10}$, $R_{11}$,] $R_{12}$ and $R_{13}$ are independently lower alkyl.

81. The process according to claim [78] *80* wherein [$R_{10}$, $R_{11}$,] $R_{12}$ and $R_{13}$ are methyl.

82. The process according to claim 71 [wherein the positively charged electron-withdrawing group is

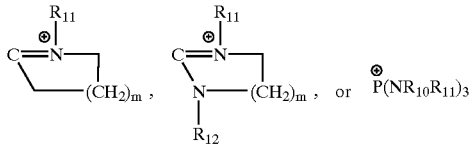

wherein [$R_{10}$, $R_{11}$,] $R_{12}$ *and* $R_{13}$ *each* are independently hydrogen, or lower alkyl or loweralkoxy lower alkyl [and m is 0 or 1].

83. The process according to claim 82 wherein [$R_{11}$ and $R_{12}$ are the same $R_{10}$ and $R_{11}$] $R_{12}$ *and* $R_{13}$ are the same.

84. The process according to claim 71 wherein [$R_3$ is

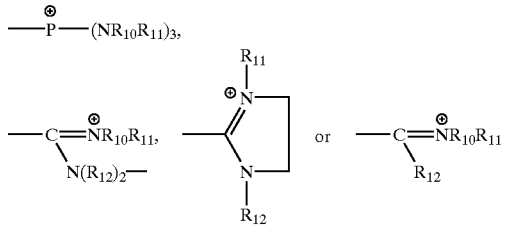

wherein $R_{10}$, $R_{11}$ and $R_{12}$ ]

$R_{12}$ *and* $R_{13}$ *each* are independently hydrogen, methyl, ethyl, propyl, butyl, pentyl, or $CH_2CH_2OCH_2CH_3$.

85. The process according to claim 84 wherein [$R_{10}$, $R_{11}$ and $R_{12}$ ] $R_{12}$ *and* $R_{13}$ are the same.

86. The process according to claim 71 wherein $R_3$ is

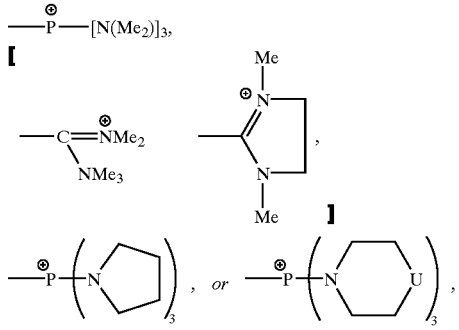

-continued

[ 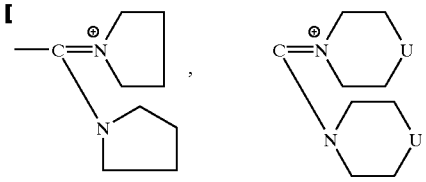 ]

wherein

U is N-ALK, $CH_2$ or O and

ALK is lower alkyl or hydrogen.

87. The process according to claim 86 wherein U is $CH_2$.

88. The process according to claim 71 wherein the compound has the formula:

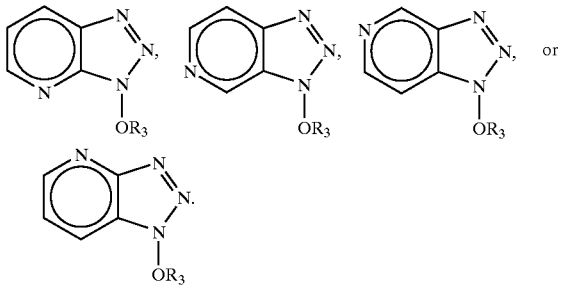

89. The process according to claim 72 wherein the compound has the formula:

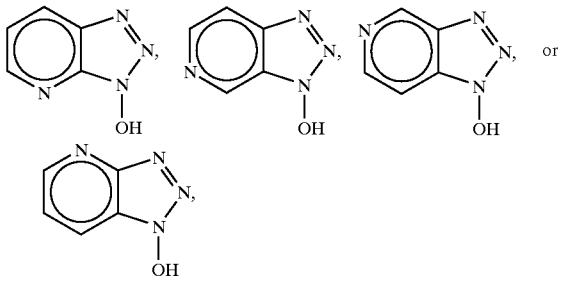

90. The process according to claim 71 wherein $R_3$ is $SO_2R_{14}$.

91. The process according to claim 88 wherein $R_3$ is [a] *the* positively charged electron-withdrawing group.

[92. The process according to claim 91 wherein the positively charged electron-withdrawing group is

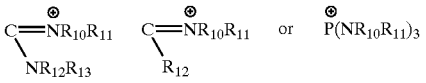

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon rings atoms or $R_{12}$ and $R_{13}$ taken together with the nitrogen atoms to which they are attached form a 5 or 6 membered nitrogen containing heterocyclic ring containing up to a total of 5 carbon ring atoms.]

93. The process according to claim [92] *91* wherein [$R_{10}$, $R_{11}$, and $R_{12}$ ] *$R_{12}$ and $R_{13}$ are each* are independently hydrogen, methyl, ethyl, propyl, butyl, pentyl or $CH_2CH_2OCH_2CH_3$.

[94. The process according to claim 88 wherein $R_3$ is

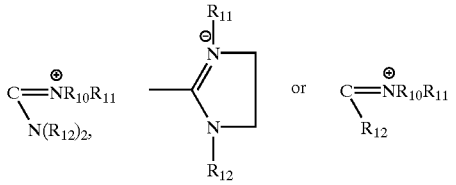

wherein $R_{10}$, $R_{11}$, $R_{12}$ are independently hydrogen, lower alkyl or lower alkoxy lower alkyl.]

95. The process according to claim 88 wherein $R_3$ is

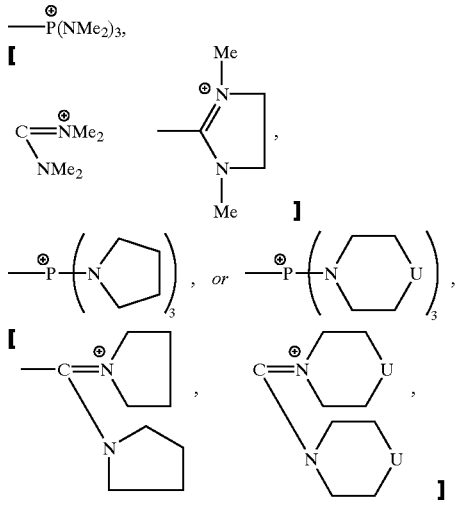

wherein

U is N-ALK, $CH_2$ or O, and ALK is lower alkyl or hydrogen.

96. The process according to claim 95 wherein U is $CH_2$ or NH.

97. The process for forming an amide comprising reacting an organic amine with a carboxylic acid in the presence of an effective amount of a compound having the formula:

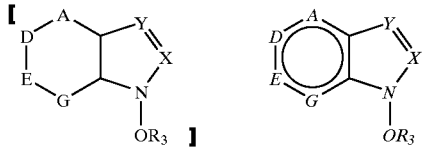

or N-oxides thereof or salts thereof wherein

D is $CR_{16}$ or N;

E is $CR_{17}$ or N;

A is $CR_{15}$ or N;

G is $CR_{18}$ or N;

and one or two of A, D, E, G is N;

$R_{15}$, $R_{16}$, $R_{17}$ and $R_{18}$ are independently hydrogen, lower alkyl or an electron-donating group;

$R_3$ $SO_2R_{14}$, or a positively charged electron-withdrawing group *of the formula* $P^{\oplus}(NR_{12}R_{13})_3$;

*each $R_{12}$ and $R_{13}$ are independently hydrogen, lower alkyl or lower alkoxy lower alkyl or $R_{12}$ and $R_{13}$ taken together with the nitrogen atom to which they are attached form a 5- or 6- membered heterocyclic ring containing up to a total of 5 ring carbon atoms*; and $R_{14}$ is lower alkyl, aryl, or aryl lower alkyl.

98. A process for forming an amide comprising reacting an organic amine with a carboxylic acid in the presence of a dehydrating reagent and an effective amount of a compound, said compound having the formula:

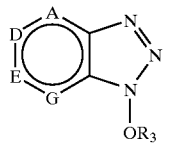

or N-oxides thereof or salts thereof, wherein

D is $CR_{16}$ or N;

E is $CR_{17}$ or N;

A is $CR_{15}$ or N;

G is $CR_{18}$ or N;

and one two of A, D, E, G is N;

$R_{15}$, $R_{16}$, $R_{17}$ and $R_{18}$ are independently hydrogen, lower alkyl or an electron-donating group; and $R_3$ is hydrogen.

99. The process according to claim 97 or 98 wherein two of A, D, E and G are N.

100. The process according to claim 97 or 98 wherein the electron-donating group is amino, lower alkyl amino, dilower-alkyl amino, hydroxy, lower alkoxy, lower aralkoxy, halo, aryl, mercapto or lower alkylthio.

101. The process according to claim 100 wherein the electron-donating group is lower dialkylamino or lower alkoxy.

102. The process according to claim 97 wherein $R_3$ is [an] *the* electron withdrawing group.

[103. The process according to claim 97 wherein $R_3$ is

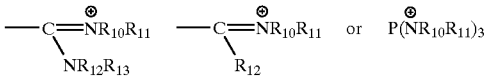

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached form a 5 or 6 membered nitrogen-containing heterocyclic ring containing up to a total of 5 carbon ring atoms.]

104. The process according to claim 97 wherein $R_3$ is

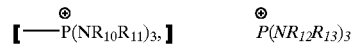

-continued

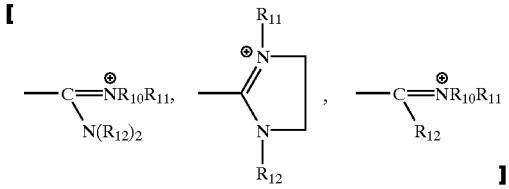

wherein

[$R_{10}$, $R_{11}$, $R_{12}$ ] *$R_{12}$ and $R_{13}$ each* are independently hydrogen, lower alkyl or lower alkoxy lower alkyl.

105. The process according to claim 97 wherein $R_3$ is

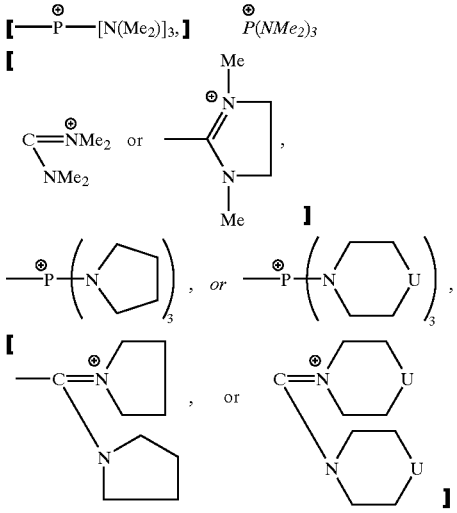

wherein

[O] *U* is N-ALK, $CH_2$ or [U] *O* and ALK is lower alkyl or hydrogen.

106. The process according to claim 105 wherein U is $CH_2$ or NH.

107. In the synthesis of a peptide wherein a first Nα-amino protected amino acid is covalently coupled to a solid phase peptide synthesis resin, the N-α-amino protecting group is cleaved off and the resulting free amino group is coupled via a peptide linkage to the carboxyl group of a second Nα-amino protected amino acid, and the cycle is repeated until the desired peptide has been obtained and then the peptide is cleaved from said resin, the improvement comprising adding to the coupling reaction an effective amount of a compound having the formula:

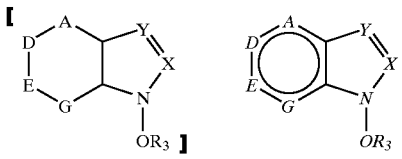

or N-oxides thereof or salts thereof;

wherein

D is $CR_{16}$ or N;

E is $CR_{17}$ or N;

A is $CR_{15}$ or N;

G is $CR_{18}$ or N;

whereby one and only are A, E, D, or G is N;

$R_{15}$, $R_{16}$, $R_{17}$, and $R_{18}$ are independently hydrogen, lower alkyl or an electron-donating group;

X is $CR_7$ or N;

Y is N or $CR_5$;

$R_7$ and $R_5$ are independently hydrogen or lower alkyl;

$R_3$ is $SO_2R_{14}$ or a positively charged electron-withdrawing group *of the formula* $P^{\oplus}(NR_{12}R_{13})_3$; and

*each* $R_{12}$ *and* $R_{13}$ *are independently hydrogen, lower alkyl or lower alkoxy lower alkyl or* $R_{12}$ *and* $R_{13}$ *taken together with the nitrogen atom to which they are attached form a 5- or 6- membered heterocyclic ring containing up to a total of 5 ring carbon atoms;*

$R_{14}$ is lower alkyl, aryl or aryl loweralkyl.

108. In the synthesis of a peptide wherein a first N-α-amino protected amino acid is covalently coupled to a solid phase peptide synthesis resin, the N-α-amino protecting group is cleaved off and the resulting free amino group is coupled via a peptide linkage to the carboxyl group of a second Nα-amino protected amino acid, and cycle is repeated until the desired peptide has been obtained and then the peptide is cleaved from said resin, the improvement comprising adding to the coupling reaction in effective amount of a compound having the formula:

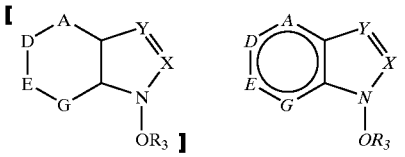

or N-oxides thereof or salts thereof;
wherein

D is $CR_{16}$ or N;

E is $CR_{17}$ or N;

A is $CR_{15}$ or N;

G is $CR_{18}$ or N;

whereby one and only one of A, E, D, or G is N;

$R_{15}$, $R_{16}$, $R_{17}$, and $R_{18}$ are independently hydrogen, lower alkyl or an electron-donating group;

X is $CR_7$ or N;

Y is N or $CR_5$;

$R_7$ and $R_5$ are independently hydrogen or lower alkyl; and $R_3$ is hydrogen.

109. The process according to claim 4 wherein $AA_1$ is an α-amino acid.

110. The process according to claim 109 wherein $AA_1$ is a naturally occurring amino acid.

111. The process according to any one *of* claims 1–4 wherein the group protecting the N-terminal amino acid or peptide is FMOC, BOC, TEOC, Aoc, Adoc, Bpoc, Azoc, Ddz, Poc, Foc, Moz, Nps, Dts, Cbz, Bspoc, Bsmoc, [Nps,] formyl, acetyl or trifluoroacetyl.

112. The process according to claim 111 wherein the group protecting the N-terminal amino acid or peptide is FMOC, BOC, Cbz, Bspoc or Bsmoc.

113. The process according to any of claims 1–3 wherein the amino compound and the carboxylic acid are independently naturally occurring amino acids.

114. A process for forming an amide containing the moiety

H, $NR_3$ comprising reacting an organic amine under amide forming conditions with an effective amount of a compound of the formula

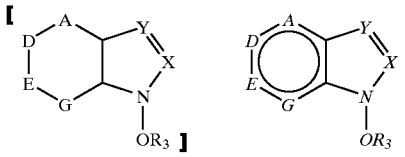

or N-oxides thereof or salt thereof;
wherein

D is $CR_{16}$ or N;

E is $CR_{17}$ or N;

A is $CR_{15}$ or N;

G is $CR_{18}$ or N;

wherein one and only one of A, E, D or G is N;

$R_{15}$, $R_{16}$, $R_{17}$, and $R_{18}$ are independently hydrogen, lower alkyl or an electron-donating group;

X is $CR_7$ or N;

Y is N or $CR_5$;

$R_7$ and $R_5$ are independently hydrogen or lower alkyl; and $R_3$ is lower alkyl carbonyl, aryl carbonyl, or aryl lower alkyl carbonyl.

115. The process according to claim 114 wherein A or G N.

116. The process according to claim 114 wherein Y is CH or N and X is CH or N.

117. The process according to claim 114 wherein the electron-donating group is amino, lower alkylamino, dilower alkylamino, hydroxy, lower alkoxy, lower aralkoxy, halo, aryl, mercapto or lower alkylthio.

118. The process according to claim 117 wherein the electron-donating group is lower dialkylamino or lower alkoxy.

119. The process according to claim 118 wherein the electron-donating group is OMe or $Me_2N$.

120. A process for forming an amide containing the moiety

H $NR_3$ comprising reacting an organic amine under amide-forming conditions with an effective amount of a compound having the formula

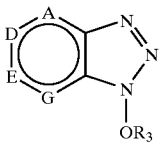

or N-oxides thereof or salts thereof;
wherein

D is $CR_{16}$ or N;

E is $CR_{17}$ or N;

A is $CR_{15}$ or N;

G is $CR_{18}$ or N;

wherein one [and only one] *or two* of A, E, D or G is N;

$R_{15}$, $R_{16}$, $R_{17}$, and $R_{18}$ are independently hydrogen, lower alkyl or an electron-donating group,

[X is $CR_7$ or N;

Y is N or $CR_5$;

$R_7$ and $R_5$ are independently hydrogen or lower alkyl;]and $R_3$ is lower alkyl carbonyl, aryl carbonyl, or aryl lower alkyl carbonyl.

121. The process according to claim 120 wherein [two] *one and only one* of A, D, E and G [are] *is* N.

122. The process according to claim 120 wherein the electron-donating group is amino, lower alkyl amino, diloweralkyl amino, hydroxy, lower alkoxy, lower aralkoxy, halo, aryl, mercapto or lower alkylthio.

123. The process according to claim 122 wherein the electron-donating group is lower dialkylamino or lower alkoxy.

124. The process according to claim 114 wherein the compound is

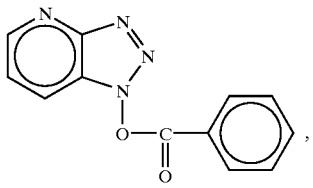

,

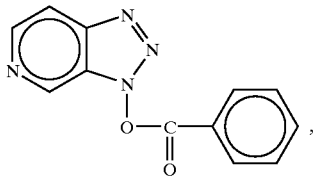

,

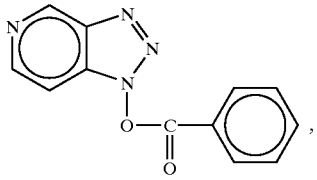

,

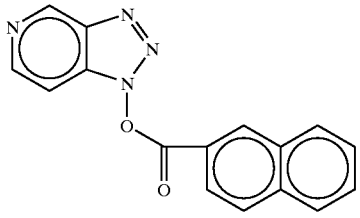

,

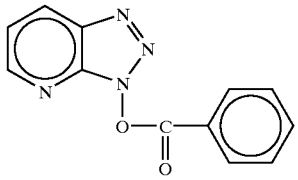

*125. A process for preparing a peptide bond comprising reacting an amino compound with a carboxylic acid in the presence of an effective amount of a compound, wherein said compound is prepared from the reaction of $R_3L$ with*

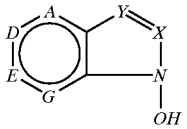

*or N-oxides thereof or salts thereof under substitution reaction conditions;*

*wherein said amino compound is an amino acid or peptide and said carboxylic acid is a N-terminal amino protected amino acid or a N-terminal amino protected peptide;*

*D is $CR_{16}$ or N;*

*E is $CR_{17}$ or N;*

*A is $CR_{15}$ or N;*

*G is $CR_{18}$ or N;*

*whereby one and only one of A, E, D, or G is N;*

*$R_{15}$, $R_{16}$, $R_{17}$ and $R_{18}$ are independently hydrogen, lower alkyl or an electron-donating group;*

*X is $CR_7$ or N;*

*Y is N or $CR_5$;*

*$R_7$ and $R_5$ are independently hydrogen or lower alkyl;*

*L is a leaving group;*

*$R_3$ is $SO_2R_{14}$ or a positively charged electron withdrawing group; and*

*$R_{14}$ is loweralkyl, aryl or aryl lower alkyl.*

*126. A process for preparing a peptide bond comprising reacting an amino compound selected from the group consisting of an amino acid and a peptide with an effective amount of compound, wherein said compound is prepared from the reaction of $R_3L$ with*

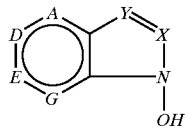

*or N-oxides thereof or salts thereof;*

*wherein*

*D is $CR_{16}$ or N;*

*E is $CR_{17}$ or N;*

*A is $CR_{15}$ or N;*

*G is $CR_{18}$ or N;*

*whereby one and only one of A, E, D, or G is N;*

*$R_{15}$, $R_{16}$, $R_{17}$, and $R_{18}$ are independently hydrogen, lower alkyl or an electron-donating group;*

*X is $CR_7$ or N;*

*L is a leaving group;*

*Y is N or $CR_5$;*

*$R_7$ and $R_5$ are independently hydrogen or lower alkyl;*

$R_3$ is $BLK_1$–$AA_1$;

*$BLK_1$ is an amino acid protecting group; and*

*$AA_1$ is an amino acid or peptide less a hydrogen on the N-terminus and an OH on the C-terminus.*

*127. The process according to claims 125 or 126 wherein A or G is N.*

*128. The process according to claims 125 or 126 wherein Y is CH or N and X is CH or N.*

*129. The process according to claims 125 or 126 wherein the electron-donating group is amino, lower alkylamino, diloweralkylamino, hydroxy, lower alkoxy, lower aralkoxy, halo, aryl, mercapto or lower alkylthio.*

*130. The process according to claim 129 wherein the electron-donating group is lower dialkylamino or lower alkoxy.*

*131. The process according to claim 130 wherein the electron-donating group is OMe or $Me_2N$.*

*132. The process according to claim 125 wherein $R_3$ is a positively charged electron withdrawing group.*

133. The process according to claim 132 wherein the positively charged electron-withdrawing group is

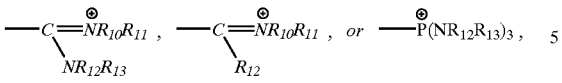

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached form a 5 or 6 membered nitrogen-containing heterocyclic ring containing up to a total of 5 carbon ring atoms.

134. The process according to claim 133 wherein $R_{10}$, $R_{11}$, $R_{12}$ and $R_{13}$ are independently hydrogen, lower alkyl or lower alkoxy lower alkyl.

135. The process according to claim 134 wherein $R_{10}$, $R_{11}$, $R_{12}$ and $R_{13}$ are independently lower alkyl.

136. The process according to claim 135 wherein $R_{10}$, $R_{11}$, $R_{12}$ and $R_{13}$ are methyl.

137. The process according to claim 132 wherein the positively charged electron-withdrawing group is

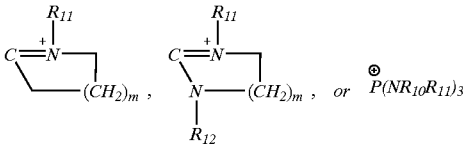

wherein $R_{10}$, $R_{11}$, $R_{12}$ are independently hydrogen, lower alkyl or loweralkoxy lower alkyl and m is 0 or 1.

138. The process according to claim 137 wherein $R_{11}$ and $R_{12}$ are the same or $R_{12}$ and $R_{13}$ are the same.

139. The process according to claim 125 wherein $R_3$ is

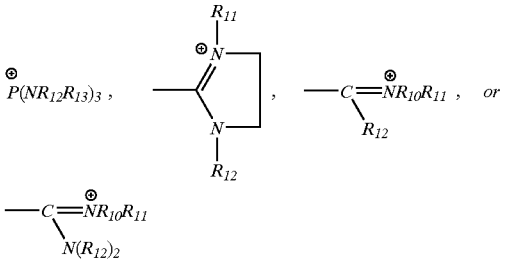

wherein $R_{10}$, $R_{11}$, $R_{12}$ and $R_{13}$ are independently hydrogen, methyl, ethyl, propyl, butyl, pentyl or $CH_2CH_2OCH_2CH_3$.

140. The process according to claim 139 wherein (a) $R_3$ is

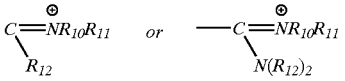

and $R_{10}$, $R_{11}$ and $R_{12}$ are the same or (b) $R_3$ is

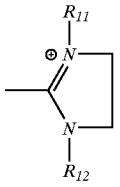

and $R_{11}$ and $R_{12}$ are the same.

141. The process according to claim 132 wherein $R_3$ is

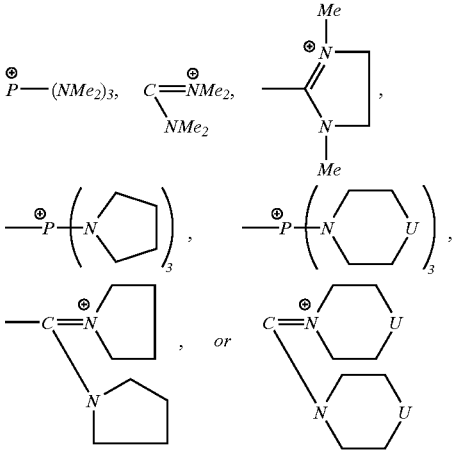

wherein

U is N-ALK, $CH_2$ or O; and

ALK is lower alkyl or hydrogen.

142. The process according to claim 141 wherein U is $CH_2$ or NH.

143. The process according to claim 126 wherein $BLK_1$ is FMOC, BOC, TEOC, Aoc, Adoc, Bpoc, Azoc, Ddz, Poc, Roc, Moz, Nps, Dts, Cbz, Bspoc, Bsmoc, formyl, acetyl, trifluoroacetyl, CLIMOC or BIMOC.

144. The process according to claim 143 wherein $BLK_1$ is Cbz, Bspoc, Bsmoc, BOC or FMOC.

145. A process for preparing a peptide bond comprising reacting an amine with a carboxylic acid in the presence of an effective amount of a compound, wherein said compound is prepared from the reaction of $R_3L$ with

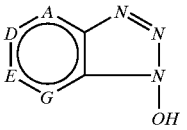

or N-oxides thereof or salts thereof under substitution reaction conditions wherein said amine is an amino acid or peptide and said carboxylic acid is a N-terminal amino protected amino acid or a N-terminal amino protected peptide;

D is $CR_{16}$ or N;

E is $CR_{17}$ or N;

A is $CR_{15}$ or N;

G is $CR_{18}$ or N;

and one or two of A, D, E, G is N;

$R_{15}$, $R_{16}$, $R_{17}$ and $R_{18}$ are independently hydrogen, lower alkyl or an electron-donating group;

L is a leaving group;

$R_3$ is $SO_2R_{14}$ or a positively charged electron-withdrawing group; and $R_{14}$ is a lower alkyl, aryl or lower alkyl.

146. A process for preparing a peptide bond comprising reacting an amino compound selected from the group consisting of an amino acid and a peptide with an effective amount of a compound, wherein said compound is prepared from the reaction of $R_3L$ with

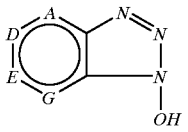

or N-oxides thereof or salts thereof wherein

D is $CR_{16}$ or N;

E is $CR_{17}$ or N;

A is $CR_{15}$ or N;

G is $CR_{18}$ or N;

and one or two of A, D, E, G is N;

$R_{15}$, $R_{16}$, $R_{17}$, and $R_{18}$ are independently hydrogen, lower alkyl or an electron-donating group;

L is a leaving group;

$R_3$ is $BLK_1$–$AA_1$;

$BLK_1$ is an amino acid protecting group; and $AA_1$ is an amino acid or peptide less a hydrogen on the N-terminus and OH on the C-terminus.

147. The process according to claim 145 or 146 wherein one of A, D, E and G is N.

148. The process according to claim 145 or 146 wherein the electron-donating group is amino, lower alkylamino, diloweralkylamino, hydroxy, lower alkoxy, lower aralkoxy, halo, aryl, mercapto or lower alkylthio.

149. The process according to claim 148 wherein the electron-donating group is lower dialkylamino or lower alkoxy.

150. The process according to claim 145 wherein $R_3$ is a positively charged electron withdrawing group.

151. The process according to claim 150 wherein $R_3$ is

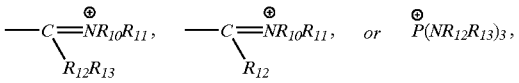

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached form a 5 or 6 membered nitrogen-containing heterocyclic ring containing up to a total of 5 carbon ring atoms.

152. The process according to claim 150 wherein $R_5$

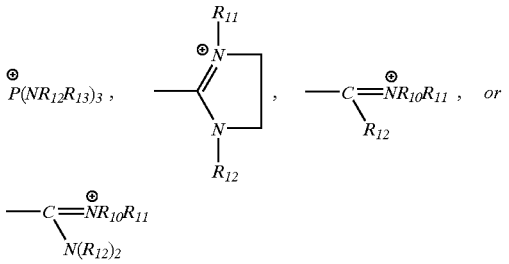

wherein $R_{10}$, $R_{11}$, and $R_{13}$ are independently hydrogen, lower alkyl or lower alkoxy lower alkyl.

153. The process according to claim 151 or 152 wherein $R_{10}$, $R_{11}$, $R_{12}$, and $R_{13}$ are independently hydrogen, methyl, ethyl, propyl, butyl, pentyl or $CH_2CH_2OCH_2CH_3$.

154. The process according to claim 153 wherein (a) $R_3$ is

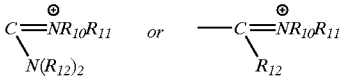

and $R_{10}$, $R_{11}$ and $R_{12}$ are the same or (b) $R_3$ is

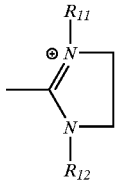

and $R_{11}$ and $R_{12}$ are the same.

155. The process according to claim 150 wherein $R_3$ is

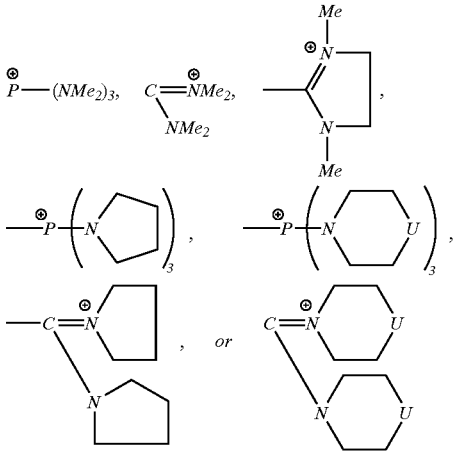

wherein

U is N-ALK, $CH_2$ or O and ALK is lower alkyl or $CH_2$ or NH.

156. The process according to claim 155 wherein U is $CH_2$ or NH.

157. The process according to claim 125 wherein $R_3L$ is reacted with

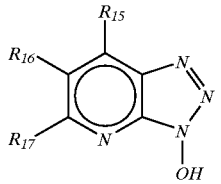

*wherein*

*one of $R_{15}$, $R_{16}$ and $R_{17}$ is hydrogen, lower alkyl or an electron donating group and the others are hydrogen.*

*158. The process according to claim 126 wherein $R_3L$ is reacted with*

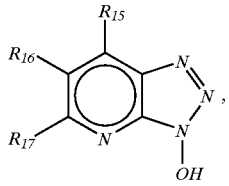

*wherein one of $R_{15}$, $R_{16}$ and $R_{17}$ is hydrogen, lower alkyl or an electron donating group and the others are hydrogen.*

*159. The process according to claim 157 wherein $R_3$ is*

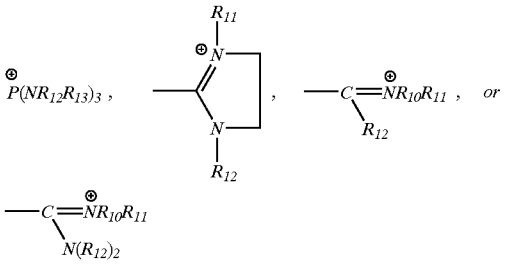

*wherein*

*$R_{10}$, $R_{11}$, and $R_{13}$ are independently hydrogen, lower alkyl or lower alkoxy lower alkyl.*

*160. The process according to claim 159 where $R_{10}$, $R_{11}$, $R_{12}$ and $R_{13}$ are independently hydrogen, methyl, ethyl, propyl, butyl, pentyl or $CH_2CH_2OCH_2CH_3$.*

*161. The process according to claim 159 or 160*

*wherein*

*(a) $R_3$ is*

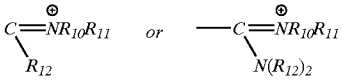

*and $R_{10}$, $R_{11}$ and $R_{12}$ are the same or*

*(b) $R_3$ is*

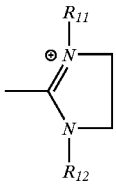

*and $R_{11}$ and $R_{12}$ are the same.*

*162. The process according to claim 157 wherein $R_3$ is*

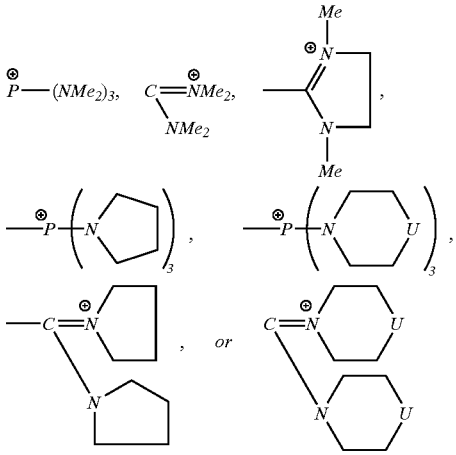

*wherein*

*U is N-ALK, $CH_2$ or O, and ALK is lower alkyl or hydrogen.*

*163. The process according to claim 146 or claim 147 wherein $R_3L$ is reacted with*

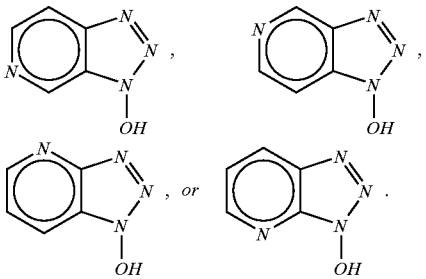

*164. The process according to claim 145 where $R_3L$ is reacted with*

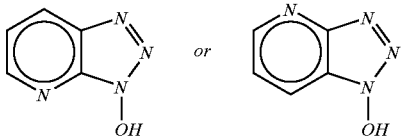

*wherein*

*$R_3$ is*

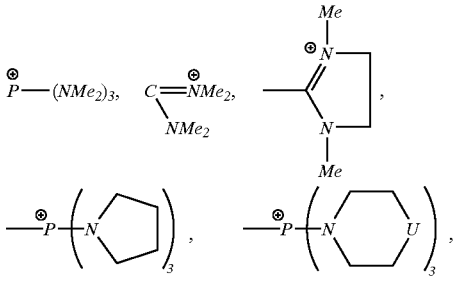

-continued

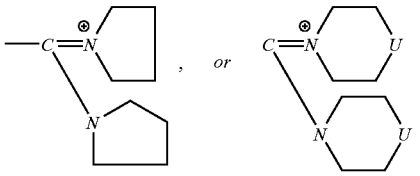

*wherein*

*U is $CH_2$, O or N-ALK and ALK is H or lower alkyl.*

*165. The process according to claim 164 wherein U is $CH_2$.*

*166. A process for forming an amide comprising reacting an organic amine and a carboxylic acid in the presence of an effective amount of a compound, wherein said compound is prepared from the reaction of $R_3L$ with a compound of the formula:*

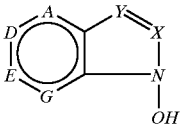

*or N-oxides thereof or salts thereof under substitution reaction conditions,*

*wherein*

*D is $CR_{16}$ or N;*

*E is $CR_{17}$ or N;*

*A is $CR_{15}$ or N;*

*G is $CR_{18}$ or N;*

*whereby one or two of A, E, D, or G is N;*

*$R_{15}$, $R_{16}$, $R_{17}$, and $R_{18}$ are independently hydrogen, lower alkyl or an electron-donating group;*

*X is $CR_7$ or N;*

*Y is N or $CR_5$;*

*$R_7$ and $R_5$ are independently hydrogen or lower alkyl;*

*$R_3$ is a positively charged electron-withdrawing group; and*

*L is a leaving group.*

*167. The process according to claim 166 wherein A or G is N.*

*168. The process according to claim 166 wherein Y is CH or N and X is CH or N.*

*169. The process according to claim 166 wherein the electron-donating group is amino, lower alkylaminodilower-alkylamino, hydroxy, lower alkoxy, lower aralkoxy, halo, aryl, mercapto or lower alkylthio.*

*170. The process according to claim 169 wherein the electron-donating group is lower dialkylamino or lower alkoxy.*

*171. The process according to claim 170 wherein the electron-donating group is OMe or $Me_2N$.*

*172. The process according to claim 166 wherein $R_3$ is a positively charged electron-withdrawing group.*

*173. The process according to claim 172 wherein the positively charged electron-withdrawing group is*

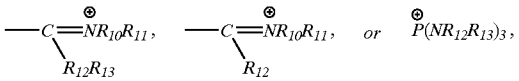

*wherein*

*$R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached form a 5 or 6 membered nitrogen-containing heterocyclic ring containing up to a total of 5 carbon ring atoms.*

*174. The process according to claim 173 wherein $R_{10}$, $R_{11}$, $R_{12}$ and $R_{13}$ are independently hydrogen, lower alkyl or lower alkoxy lower alkyl.*

*175. The process according to 173 wherein $R_{10}$, $R_{11}$, $R_{12}$ and $R_{13}$ are independently lower alkyl.*

*176. The process according to claim 175 wherein $R_{10}$, $R_{11}$, $R_{12}$ and $R_{13}$ are methyl.*

*177. The process according to claim 172 wherein the positively charged electron-withdrawing group is*

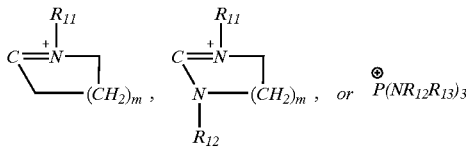

*wherein*

*$R_{11}$, $R_{12}$ and $R_{13}$ are independently hydrogen, or lower alkyl or loweralkoxy lower alkyl and m is 0 or 1.*

*178. The process according to claim 177 wherein $R_{11}$ and $R_{12}$ are the same or $R_{12}$ and $R_{13}$ are the same.*

*179. The process according to claim 172 wherein $R_3$ is*

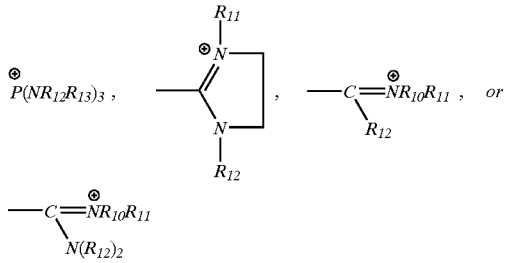

*wherein*

*$R_{11}$, $R_{12}$ and $R_{13}$ are independently hydrogen, methyl, ethyl, propyl, butyl, pentyl, or $CH_2CH_2OCH_2CH_3$.*

*180. The process according to claim 179 wherein (a) $R_3$ is*

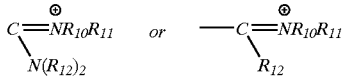

*and $R_{10}$, $R_{11}$ and $R_{12}$ are the same or*

*(b) $R_3$ is*

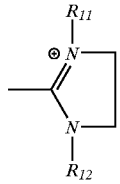

*and $R_{11}$ and $R_{12}$ are the same.*

181. The process according to claim 172 wherein $R_3$ is

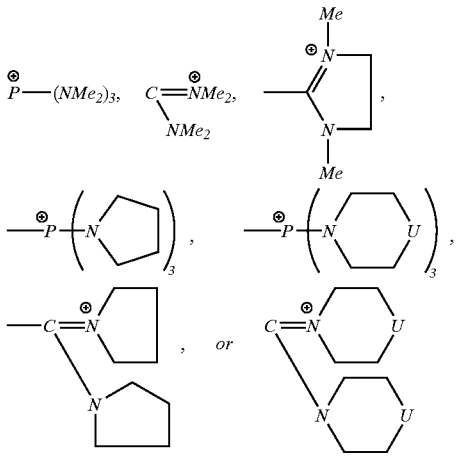

wherein

U is N-ALK, $CH_2$ or O and

ALK is lower alkyl or hydrogen.

182. The process according to claim 181 wherein U is $CH_2$.

183. The process according to claim 165 or 166 wherein $R_3L$ is reacted with

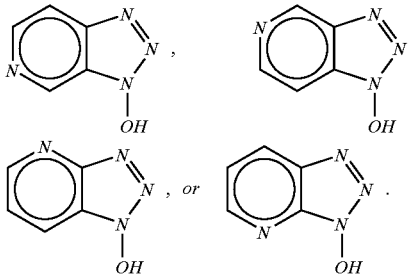

184. The process according to claim 183 wherein $R_3$ is

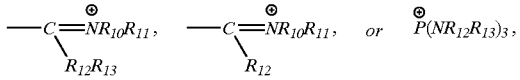

wherein $R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached form a 5 or 6 membered nitrogen containing heterocyclic ring containing up to a total of 5 carbon ring atoms.

185. The process according to claim 184 wherein $R_{10}$, $R_{11}$, $R_{12}$ and $R_{13}$ are independently hydrogen, methyl, ethyl, propyl, butyl, pentyl or $CH_2CH_2OCH_2CH_3$.

186. The process according to claim 183 wherein $R_3$ is

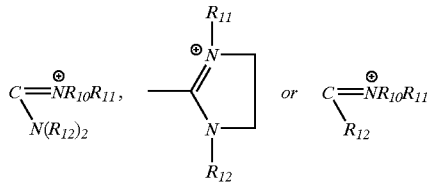

wherein $R_{10}$, $R_{11}$, $R_{12}$ are independently hydrogen, lower alkyl or lower alkoxy lower alkyl.

187. The process according to claim 183 wherein $R_3$ is

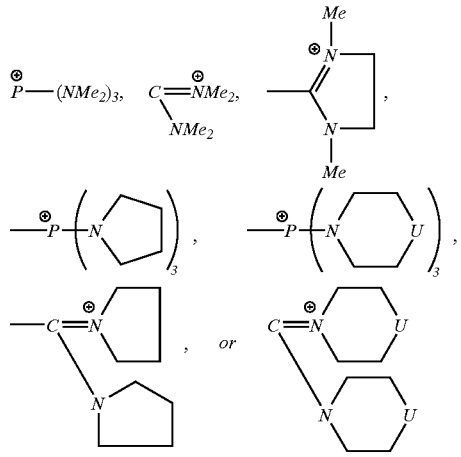

wherein

U is N-ALK, $CH_2$ or O, and ALK is lower alkyl or hydrogen.

188. The process according to claim 187 wherein U is $CH_2$ or NH.

189. A process for forming an amide comprising reacting an organic amine with a carboxylic acid in the presence of an effective amount of a compound, wherein said compound is prepared from the reaction of $R_3L$ with

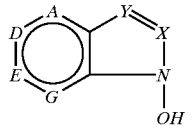

or N-oxides thereof or salts thereof under substitution reaction conditions wherein D is $CR_{16}$ or N;

E is $CR_{17}$ or N;

A is $CR_{15}$ or N;

G is $CR_{18}$ or N;

an one or two of A, D, E, G is N;

$R_{15}$, $R_{16}$, $R_{17}$ and $R_{18}$ are independently hydrogen, lower alkyl or an electron-donating group;

$R_3$ is $SO_2R_{14}$ or a positively charged electron-withdrawing group;

L is a leaving group; and $R_{14}$ is loweralkyl, aryl or lower arylalkyl.

190. The process according to claim 189 for forming an amide comprising reacting an organic amine with a car-

*boxylic acid in the presence of a dehydrating reagent and an effective amount of a compound, said compound prepared from the reaction of $R_3L$ with*

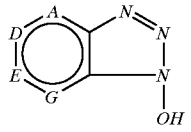

*or N-oxides thereof or salts thereof, under substitution reaction conditions.*

*191. The process according to claim 189 or 190 wherein one of A, D, E and G is N.*

*192. The process according to claim 189 or 190 wherein the electron-donating group is amino, lower alkyl amino, diloweralkyl amino, hydroxy, lower alkoxy, lower aralkoxy, halo, aryl, mercapto or lower alkylthio.*

*193. The process according to claim 192 wherein the electron-donating group is lower dialkylamino or lower alkoxy.*

*194. The process according to claim 189 or 190 wherein $R_3$ is*

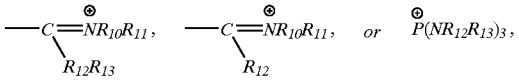

*wherein*

*$R_{10}$, $R_{11}$, $R_{12}$ and $R_{13}$ are independently hydrogen, lower alkyl, lower alkoxy lower alkyl or $R_{10}$ and $R_{11}$ taken together with the atoms to which they are attached form a ring containing up to 6 ring atoms and up to a total of 5 carbon ring atoms or $R_{12}$ and $R_{13}$ taken together with the nitrogen atoms to which they are attached form a 5 or 6 membered nitrogen-containing heterocyclic ring containing up to a total of 5 carbon ring atoms.*

*195. The process according to claim 189 or 190 wherein $R_3$ is*

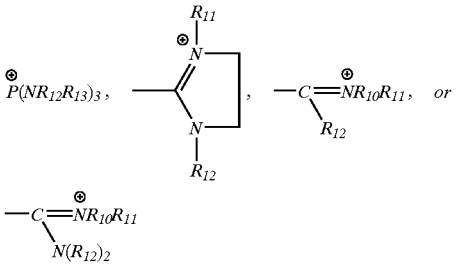

*wherein*

*$R_{10}$, $R_{11}$, $R_{12}$ and $R_{13}$ are independently hydrogen, lower alkyl or lower alkoxy lower alkyl.*

*196. The process according to claim 189 or 190 wherein $R_3$ is*

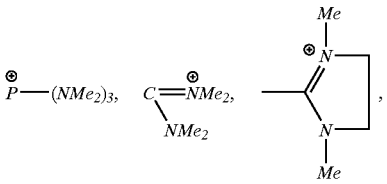

-continued

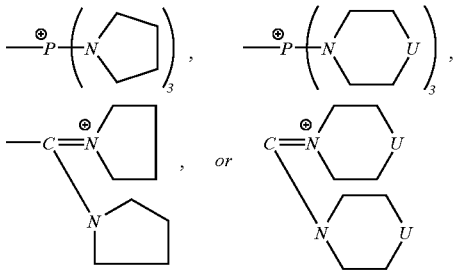

*wherein*

*O is N-ALK, $CH_2$ or U and ALK is lower alkyl or hydrogen.*

*197. The process according to claim 196 wherein U is $CH_2$ or NH.*

*198. In the synthesis of a peptide wherein a first N-α-amino protected amino acid is covalently coupled to a solid phase peptide synthesis resin, the N-α-amino protecting group is cleaved off and the resulting free amino group is coupled via a peptide linkage to the carboxylic group of a second N-α-amino protected amino acid, and the cycle is repeated until the desired peptide has been obtained and then the peptide is cleaved from said resin, the improvement comprising adding to the coupling reaction an effective amount of a compound formed from the reaction of $R_3L$ with a compound of the formula:*

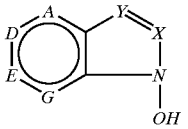

*or N-oxides thereof or salts thereof under substitution reaction conditions;*

*wherein*

*D is $CR_{16}$ or N;*

*E is $CR_{17}$ or N;*

*A is $CR_{15}$ or N;*

*G is $CR_{18}$ or N;*

*whereby one and only one of A, E, D, or G is N;*

*$R_{15}$, $R_{16}$, $R_{17}$, and $R_{18}$ are independently hydrogen, lower alkyl or an electron-donating group;*

*X is $CR_7$ or N;*

*Y is N or $CR_5$;*

*$R_7$ and $R_5$ are independently hydrogen or lower alkyl;*

*$R_3$ is $SO_2R_{14}$ or a positively charged electron-withdrawing group;*

*L is a leaving group; and*

*$R_{14}$ is lower alkyl, aryl, or aryl loweralkyl.*

*199. The process according to claim 126 wherein $AA_1$ is an α-amino acid.*

*200. The process according to 199 wherein $AA_1$ is a naturally occurring amino acid.*

*201. The process according to claim 125 or 126 wherein the amino compound and the carboxylic acid are independently naturally occurring amino acids.*

*202. A process for forming an amide containing the moiety*

*H*

*$NR_3$*

*comprising reacting an organic amine under amide forming conditions with an effective amount of a compound prepared by reacting $R_3L$ with*

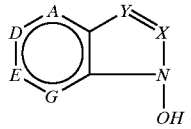

*or N-oxides thereof or salts thereof;*

*wherein*

*D is* $CR_{16}$ *or N;*

*E is* $CR_{17}$ *or N;*

*A is* $CR_{15}$ *or N;*

*G is* $CR_{18}$ *or N;*

*wherein*

*one and only one of A, E, D or G is N;*

$R_{15}$, $R_{16}$, $R_{17}$ *and* $R_{18}$ *are independently hydrogen, lower alkyl or an electron-donating group;*

*X is* $CR_7$ *or N;*

*Y is N or* $CR_5$;

$R_7$ *and* $R_5$ *are independently hydrogen or lower alkyl; and*

$R_3$ *is lower alkyl carbonyl, aryl carbonyl, or aryl lower alkyl carbonyl; and*

*L is a leaving group.*

*203. The process according to claim 202 wherein A or G is N.*

*204. The process according to claim 202 wherein Y is CH or N and X is CH or N.*

*205. The process according to claim 202 wherein the electron-donating group is amino, lower alkylamino, diloweralkylamino, hydroxy, lower alkoxy, lower aralkoxy, halo, aryl, mercapto or lower alkylthio.*

*206. The process according to claim 205 wherein the electron-donating group is lower dialkylamino or lower alkoxy.*

*207. The process according to claim 206 wherein the electron-donating group is* $Me_2N$ or OMe.

*208. The process for forming an amide containing the moiety*

*H*

$NR_3$

*comprising reacting an organic amine under amide-forming conditions with an effective amount of a compound prepared by reacting* $R_3L$ *with*

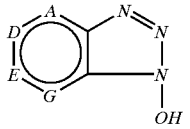

*or N-oxides thereof or salts thereof;*

*wherein*

*D is* $CR_{16}$ *or N;*

*E is* $CR_{17}$ *or N;*

*A is* $CR_{15}$ *or N;*

*G is* $CR_{18}$ *or N;*

*wherein*

*one or two of A, E, D or G is N;*

$R_{15}$, $R_{16}$, $R_{17}$ *and* $R_{18}$ *are independently hydrogen, lower alkyl or an electron-donating group;*

*X is* $CR_7$ *or N;*

*Y is N or* $CR_5$;

*L is a leaving group;*

$R_7$ *and* $R_5$ *are independently hydrogen or lower alkyl; and*

$R_3$ *is lower alkyl carbonyl, aryl carbonyl, or aryl lower alkyl carbonyl.*

*209. The process according to claim 208 wherein one of A, D, E and G is N.*

*210. The process according to claim 200 wherein the electron-donating group is amino, lower alkyl amino, diloweralkyl amino, hydroxy, lower alkoxy, lower aralkoxy, halo, aryl, mercapto or lower alkylthio.*

*211. The process according to claim 210 wherein the electron-donating group is lower dialkylamino or lower alkoxy.*

*212. The process according to claim 145 or 166 wherein the compound is formed by reacting 1-hydroxy-7-axabenzotriazole with* $R_3L$, *wherein* $R_3$ *is 1,1,3,3-tetramethyluronium salt and L is a leaving group.*

*213. The process according to claim 212 wherein the leaving group is a halide.*

* * * * *

UNITED STATES PATENT AND TRADEMARK OFFICE

CERTIFICATE OF CORRECTION

PATENT NO. : RE 38,073 E
DATED : April 8, 2003
INVENTOR(S) : Louis A. Carpino

It is certified that error appears in the above-identified patent and that said Letters Patent is hereby corrected as shown below:

Title page,
Item [73], Assignee, "Corporations" should read -- Corporation --

Signed and Sealed this

Third Day of February, 2004

JON W. DUDAS
*Acting Director of the United States Patent and Trademark Office*